United States Patent
Bedenbaugh

(10) Patent No.: US 8,500,752 B2
(45) Date of Patent: *Aug. 6, 2013

(54) ANCHORING APPARATUS AND METHODS FOR USE

(75) Inventor: Purvis Bedenbaugh, Greenville, NC (US)

(73) Assignee: Cranial Medical Systems, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/234,005

(22) Filed: Sep. 15, 2011

(65) Prior Publication Data

US 2012/0238992 A1 Sep. 20, 2012

Related U.S. Application Data

(62) Division of application No. 12/056,752, filed on Mar. 27, 2008, now Pat. No. 8,038,685.

(60) Provisional application No. 60/908,367, filed on Mar. 27, 2007.

(51) Int. Cl.
*A61B 19/00* (2006.01)

(52) U.S. Cl.
USPC ............ 606/130; 606/129; 607/115; 600/378

(58) Field of Classification Search
USPC .......... 600/378; 606/129–130; 607/115–116
See application file for complete search history.

(56) References Cited

U.S. PATENT DOCUMENTS

| | | | |
|---|---|---|---|
| 3,760,811 A * | 9/1973 | Andrew | 128/207.17 |
| 4,328,813 A | 5/1982 | Ray | |
| 5,464,446 A | 11/1995 | Dreessen et al. | |
| 6,044,304 A | 3/2000 | Baudino | |
| 6,134,477 A | 10/2000 | Knuteson | |
| 6,482,182 B1 | 11/2002 | Carroll et al. | |
| 6,662,035 B2 | 12/2003 | Sochor | |
| 6,819,958 B2 | 11/2004 | Weiner et al. | |

(Continued)

FOREIGN PATENT DOCUMENTS

| | | |
|---|---|---|
| WO | WO 2004/026161 A2 | 4/2004 |
| WO | WO 2004/026161 A3 | 8/2004 |
| WO | WO 2008/054691 A2 | 5/2008 |
| WO | WO 2008/054691 A3 | 6/2008 |

OTHER PUBLICATIONS

International search report and written opinion dated Aug. 8, 2008 for PCT/US2008/058484.

(Continued)

*Primary Examiner* — Rex R Holmes

(74) *Attorney, Agent, or Firm* — Wilson, Sonsini, Goodrich & Rosati

(57) ABSTRACT

An apparatus for securing an implantable lead within tissue of a patient includes a base adapted to be secured to a patient's skull adjacent a craniotomy. The base has an upper surface and a lower surface with a central passage therebetween. The central passage is adapted to receive the implantable lead therethrough. The apparatus also has a cover that is releasably coupled to the base so as to substantially cover the central passage and capture the implantable lead therebetween. A first rotating member is also coupled with the base and the first member is rotationally movable so as to meet and engage the implantable lead at a plurality of positions within the central passage.

20 Claims, 26 Drawing Sheets

U.S. PATENT DOCUMENTS

| | | |
|---|---|---|
| 7,004,948 B1 | 2/2006 | Pianca et al. |
| 2004/0267284 A1 | 12/2004 | Parmer et al. |
| 2005/0182423 A1* | 8/2005 | Schulte et al. ............ 606/130 |
| 2005/0182464 A1 | 8/2005 | Schulte et al. |
| 2005/0192594 A1 | 9/2005 | Skakoon et al. |
| 2008/0172068 A1 | 7/2008 | Adams et al. |
| 2009/0088826 A1 | 4/2009 | Bedenbaugh |

OTHER PUBLICATIONS

European search report dated Jan. 15, 2013 for EP Application No. 08732953.8.

* cited by examiner

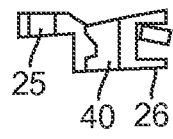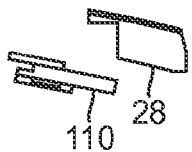
FIG. 8G
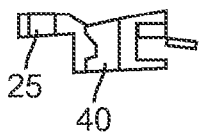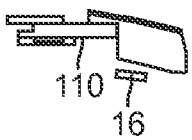
FIG. 8H
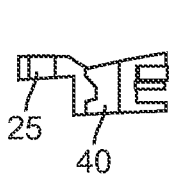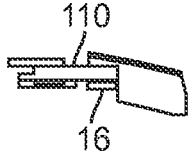
FIG. 8I
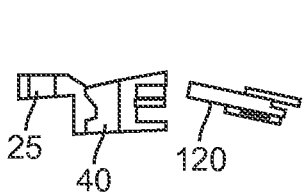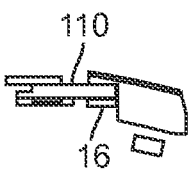
FIG. 8J
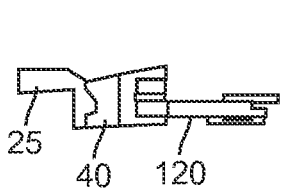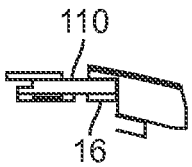
FIG. 8K
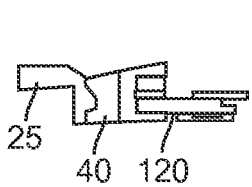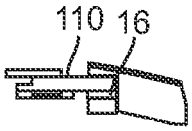
FIG. 8L
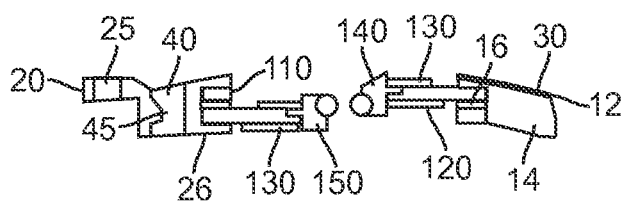
FIG. 8M

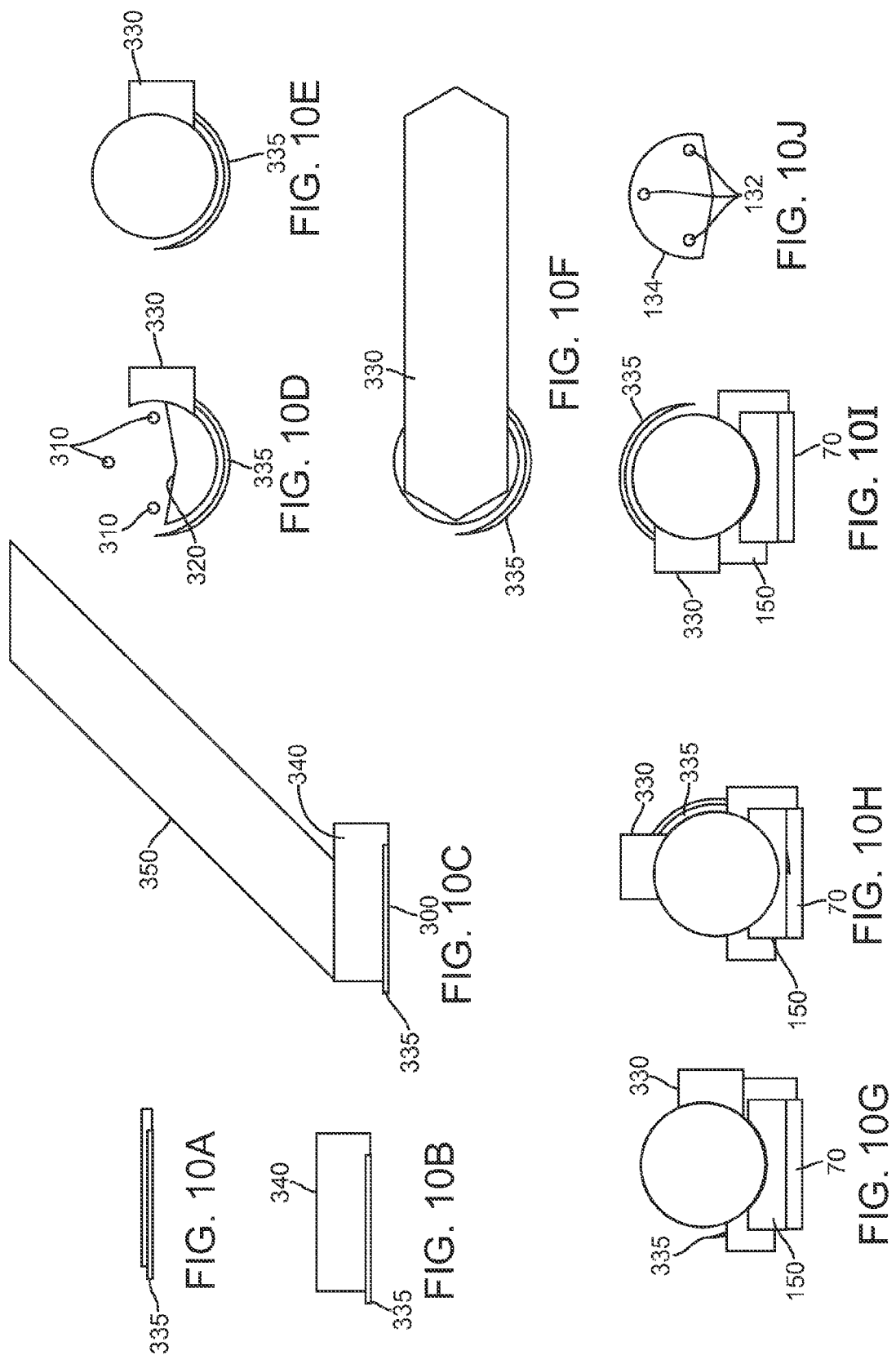

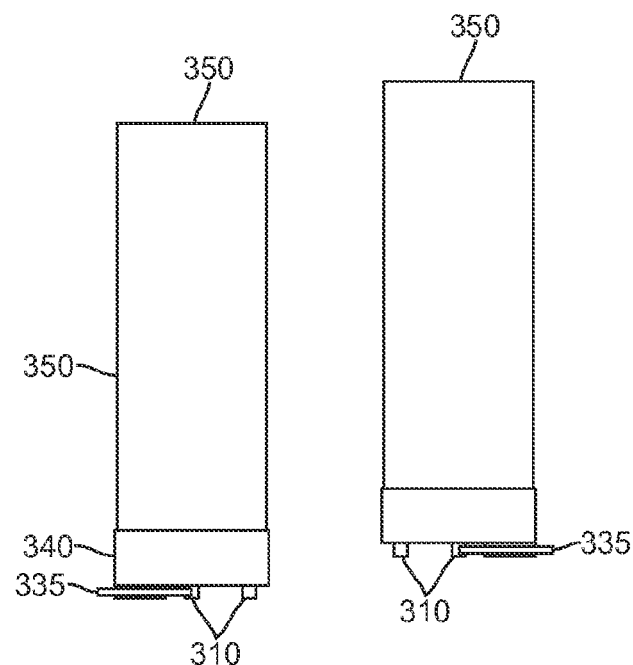
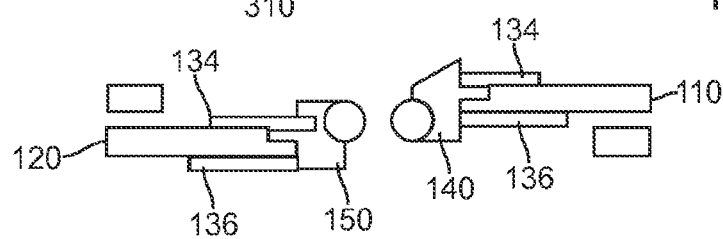
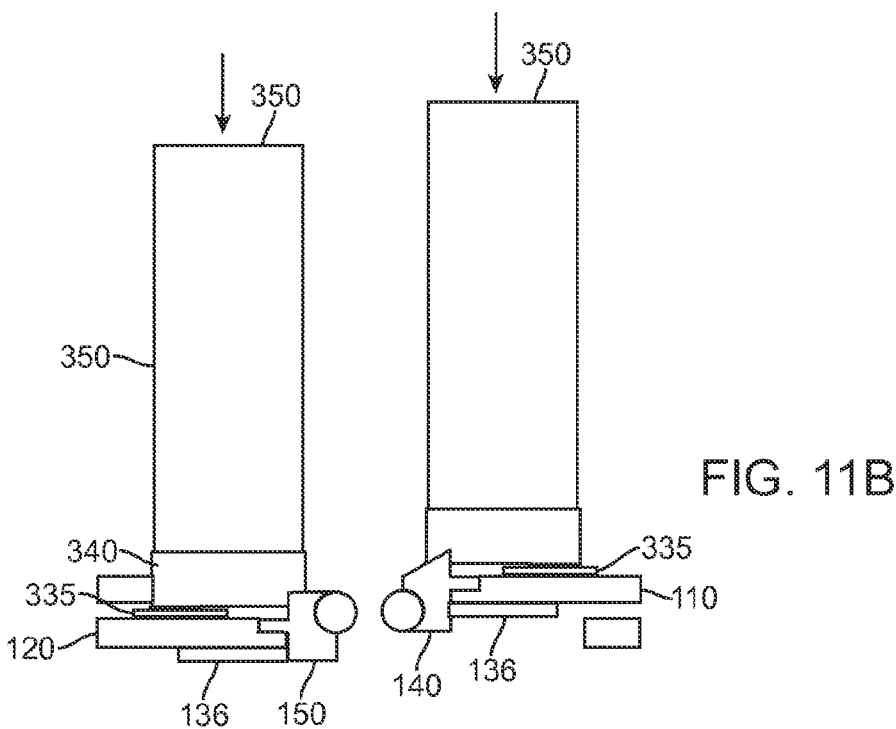
FIG. 11A
FIG. 11B

ANCHORING APPARATUS AND METHODS FOR USE

CROSS-REFERENCE

This application is a divisional of U.S. patent application Ser. No. 12/056,752, now U.S. Pat. No. 8,038,685, filed on Mar. 27, 2008, which is a non-provisional of, and claims the benefit of U.S. Provisional Patent Application No. 60/908,367, filed Mar. 27, 2007; the entire contents of each of which are incorporated herein by reference.

BACKGROUND OF THE INVENTION

1. Field of the Invention

This invention relates generally to medical apparatus and methods, more specifically to instrument immobilizers and even more specifically, but not by way of limitation to an apparatus and methods for anchoring an intracranial probe or lead to the cranium.

Implanting medical devices within the cranium is an increasingly important approach for treatment of disorders such as Parkinson's Disease, essential tremor and dystonia. This approach may also be used to treat a wide array of neuropsychiatric problems, such as depression, epilepsy, obsessive compulsive disorder, obesity and chronic pain. Most of these devices interact with the brain by delivering current through an implanted probe to modulate brain activity. In addition, infusion of drugs through a permanently implanted probe has been proposed as a primary treatment, or as an adjunctive treatment to electrical stimulation, for Alzheimer's and Parkinson's Diseases, among others.

As part of the implant procedure, the probe must be stabilized in the brain. Ideally, any prosthetic device is attached directly to the tissue on which it operates, in this case, the brain. Direct attachment of electrical and chemical probes to brain tissue is impractical. A more easily implementable solution is a system of flexible probes that bend and float with the brain as the brain moves within the cranial cavity. Such probes are secured to the cranium. In this manner, mechanical forces from outside the cranium are prevented from acting on the brain-to-probe interface.

There are a number of current techniques for securing a probe to the cranium. For example, in one approach, a permanently implanted probe is fixed by a sliding door which closes to form a slot just wide enough to slightly compress and grip the body of the probe. A common feature of such devices is that they grip the probe somewhere within the craniotomy opening, and that the slot has a fixed orientation relative to the cranium.

In another approach, the probe passes through a narrow aperture at the center of a craniotomy opening The probe is held in place by a surgeon as it is bent over into a slot leading to the exit from the device. Hinged arms swing into place to narrow the slot and anchor the probe within the slot.

Current anchoring devices are typically positioned over the craniotomy opening, and they are attached to the cranium with several peripheral screws. An implantable lead is placed through the cranial opening and the lead is gripped by two opposing thin bars. In some cases, it is possible to damage the lead by crushing it between the thin bars. It would therefore be desirable to grip the lead with wider bars to more evenly distribute the gripping force over a greater axial length of the implantable lead. It would also be desirable to provide a more stable mounting for the skull-mounted portion of the anchoring device. Additionally, current devices often have a small opening for receiving the lead and thus it would be desirable to provide an anchoring device having a wider opening for the lead, to permit adjustment of lead position for optimal placement, especially when using a large multi-channel probe array, a feature shared by only a few currently available anchoring systems.

2. Description of the Background Art

Prior patents and publications describing anchors for cranial probes include: U.S. Pat. Nos. 4,328,813; 5,464,446; 6,044,304; 2004/0267284; 2005/0192594; and WO 2004/026161.

SUMMARY OF THE INVENTION

The invention generally provides an anchor for securing an implantable lead within tissues in a patient. The terms "lead" and "probe" will be used interchangeably with one another in this disclosure, as will the terms "anchor base" and "cylinder." Often the lead may comprise an electrode or a catheter, and the lead is often implanted into brain tissue through a craniotomy in the patient's skull. A current and/or therapeutic agent may be delivered through the lead to the tissue and the anchor is usually composed of materials that are compatible with magnetic resonance imaging. The anchor may be fabricated from metals that do not interfere with MRI and/or polymers such as polyphenylene sulfide, polyetheretherketone (PEEK), polyetherimide, polyimide, polysulfone and the like.

In a first aspect of the present invention an apparatus for securing an implantable lead within tissue of a patient comprises a base that is adapted to be secured to a patient's skull adjacent a craniotomy. The base has an upper surface, a lower surface and a central passage therebetween which is adapted to receive the implantable lead. The apparatus also includes a cover that can be releasably coupled to the base so as to substantially cover the central passage and also to capture the lead therebetween. A first rotating member or door, is coupled with the base and is rotationally movable so as to meet and engage the lead at a plurality of positions within the central passage. Rotating the door also adjusts the position of an opening within the central passage in which the lead may pass through and also closes or reduces the size of the central passage while still allowing the lead to pass therethrough.

Often, the first rotating member comprises a removable insert that is adapted to releasably grip the lead and that may be received in a recessed region of the rotating member. The removable insert is usually adapted to be removably coupled to the first rotating member with a rotationally actuated tool that may be coupled to the first rotating member. The first rotating member may have a surface defining a wedge shaped or indented region that is adapted to receive and align the tool.

The apparatus may have a pin or rivet engaged with the first rotating member that secures the first rotating member to the base while allowing rotation of the first rotating member relative to the base. The first rotating member may also have a surface that defines a receptacle that is adapted to receive a tool for turning the first rotating member into a desired position so as to engage the lead and fix the lead into a position. The first rotating member may further comprise a resilient end that is adapted to releasably grip the lead. The resilient end may lie in the same plane as the first rotating member and may be composed of an elastomer. The resilient end often is constructed with a substantially solid core while sometimes it may be porous. Often the resilient end comprises surface features that are adapted to capture the lead. The surface features may include a plurality of convex or concave regions adjacent to one another or the surface features may be scallops. Sometimes the surface features may comprise a plurality of resilient fingers that extend outward from the resilient end. The surface features may also comprise combinations thereof.

The apparatus may further comprise a ratchet mechanism that is adapted to restrict the first rotating member to motion in one direction. Often the apparatus also comprises a fixing element such as a set screw that is adapted to immobilize the first rotating member. The apparatus also often comprises a second rotating member that is coupled with the base and a spacer may be used to separate the first and second rotating members from one another. The second rotating member is rotationally movable so as to meet and engage the lead at a plurality of positions within the central passage. Rotating the second door also adjusts the position of an opening within the central passage in which the lead may pass through and also closes or reduces the size of the central passage while still allowing the lead to pass therethrough. Usually, the first and second rotating members are movable independently of one another and they may be retained in the base with a retaining member such as a ring. Also, the first and second rotating members may lie in the base adjacent to one another. Sometimes the second rotating member comprises a removable insert that is adapted to releasably grip the lead. The insert on the second rotating member may take the same form as the insert on the first rotating member. Often the resilient end on the first rotating member lies in a plane between the first and second rotating members.

The apparatus may further comprise a locking mechanism coupled with the first and second rotating members. The locking mechanism locks the first and second members together thereby preventing relative motion therebetween. The locking mechanism may be a detent and comprise a protuberance on either the first or second rotating member and a receptacle for receiving the protuberance on the other rotating member. These features allow the rotating members to snap into position with one another thereby ensuring the lead is gripped therebetween.

Often, the apparatus further comprises one or more tabs that extend radially outward from the base. The tabs are adapted to be secured to the skull adjacent the craniotomy. The tabs often define apertures that can receive a fastener such as a screw, thereby securing the base adjacent the craniotomy.

Sometimes the base is cylindrical and may be sized to fit at least partially within the craniotomy, and at least a portion of the base may be securely press fit into the craniotomy. The base may comprise a discrete upper and a discrete lower portion that are fastened together, or the base may be of unitary construction. The base may be recessed at least partially into the craniotomy, or the lower surface of the base may sit substantially flush with the top of the skull. The base may also have one or more receptacles that are adapted to releasably receive at least a portion of the cover. Often, the upper surface of the base defines one or more channels that are sized and shaped to accept the lead after the lead has been disposed therein. The base may also be adapted to receive and retain other surgical instruments such as instrument positioning guides or other reference devices often used during neurosurgery. These other surgical instruments may releasably lock with a flange in the base, a retaining member in the base or any other portion of the base or components therein.

Often the cover is adapted to be removably coupled to the base. Sometimes the cover comprises one or more legs that are adapted to releasably snap fit into engagement with the base. Alternatively, the legs may be disposed on the base or on a retaining member that fits in the base. The cover may have a surface that defines one or more channels that are sized and shaped to accept the lead after it has been disposed therein.

One or more plugs may be placed into the channels or a gasket may be disposed between the cover and the base in order to seal any gaps therebetween.

In another aspect of the present invention, a system for securing an implantable lead within tissue of a patient comprises an apparatus for securing the implantable lead within tissue. The apparatus comprises a base adapted to be secured to a patient's skull adjacent a craniotomy, the base having an upper and lower surface and a central passage therebetween. The implantable lead is often disposed in the central passage. The apparatus also comprises a first rotating member coupled with the base and having a removable insert adapted to engage the lead. A retaining pin may couple the insert with the first rotating member. The first rotating member is rotationally movable so as to meet and engage the lead at a plurality of positions within the central passage. Rotating the door also adjusts the position of an opening within the central passage in which the lead may pass through and also closes or reduces the size of the central passage while still allowing the lead to pass therethrough. The system also includes a tool having a proximal end, a distal end and a handle, the tool being adapted to introduce and remove the removable insert to or from the first rotating member.

Often the tool also comprises a pin disposed near the distal end that is adapted to retain the insert when the insert is decoupled from the first rotating member. The tool is usually adapted to be rotated so as to simultaneously engage the insert and withdraw the retaining pin from the insert. The tool may have an angled surface that facilitates seating of the tool against the first rotating member.

The system may also include a cover that can be coupled to the base so as to substantially cover the central passage and also to capture the lead therebetween. The system may also comprise a potting material that is used to fill gaps between the base and the craniotomy in order to reduce or eliminate leakage of body fluids, such as cerebral spinal fluid (CSF), from around the base.

In another aspect of the present invention, a method of securing an implantable lead into tissue of a patient comprises positioning a base having an upper surface, a lower surface and a central passage therethrough, adjacent a craniotomy in a skull of a patient. The base may be secured adjacent the craniotomy and to the skull and an implantable lead is inserted through the central passage into the tissue. Rotating a first rotating member that is coupled to the base moves the rotating member so that it meets and engages the implantable lead at a plurality of positions within the central passage.

The method may also comprise the step of rotating a second rotating member that is also coupled to the base so as to meet and engage the lead at a plurality of positions within the central passage thereby securing the lead in the tissue. Rotating the second door also adjusts the position of an opening within the central passage in which the lead may pass through and also closes or reduces the size of the central passage while still allowing the lead to pass therethrough. The method may also include rotationally adjusting the first and second rotating members in order to capture the lead therebetween or to release the lead therefrom. Often the method includes attaching and/or removing an insert that is adapted to engage the lead and that is coupled to the first or second rotating members.

The method may also comprise inserting one or both of the two rotating members into a secure base ring intraoperatively. In early stages of the lead implantation procedure, a wide lumen is available. After the lead is placed, an opening in such rotating members allows them to pass around the lead and rest in the base, and grip the lead. The method may further comprise retaining the two rotating members within the base by interlocking a retaining member placed over the rotating members and within the base, thereby restricting axial movement of the rotating members relative to the base.

Sometimes securing the base comprises press fitting at least a portion of the base into the craniotomy and often securing the base comprises coupling the base to the skull adjacent the craniotomy with a fastener such as a screw. Sometimes securing the base comprises recessing at least a portion of the base in the craniotomy, or the base may be coupled adjacent the craniotomy such that a bottom surface of the base is substantially flush with the craniotomy.

Usually, a cover is engaged with the base so as to substantially cover the central passage and capture the implantable lead therebetween. The cover and/or base may have channels which can accept the lead after being positioned therein. Often the first and second rotating members are locked and this may be accomplished by threadably engaging the rotating members with a set screw or by using detents in order to prevent relative motion therebetween. Sometimes, the lead may be bent into a channel that is defined by a top surface of the base and a potting material may be applied in order to fill gaps between the base and the craniotomy, thereby reducing or eliminating leakage of body fluids such as CSF from around the base.

These and other embodiments are described in further details in the following description related to the appended drawing figures.

BRIEF DESCRIPTION OF THE DRAWINGS

FIGS. 8D-8M show various components in various stages of assembly with the anchor base of FIGS. 8A-8C.

FIGS. 10A-10J show the use of a tool for placement and removal of inserts into the rotating doors.

FIGS. 11A-11D show side views of a tool as it us used to insert, place, attach and detach inserts into the anchor.

DETAILED DESCRIPTION OF THE INVENTION

Figure 1A:
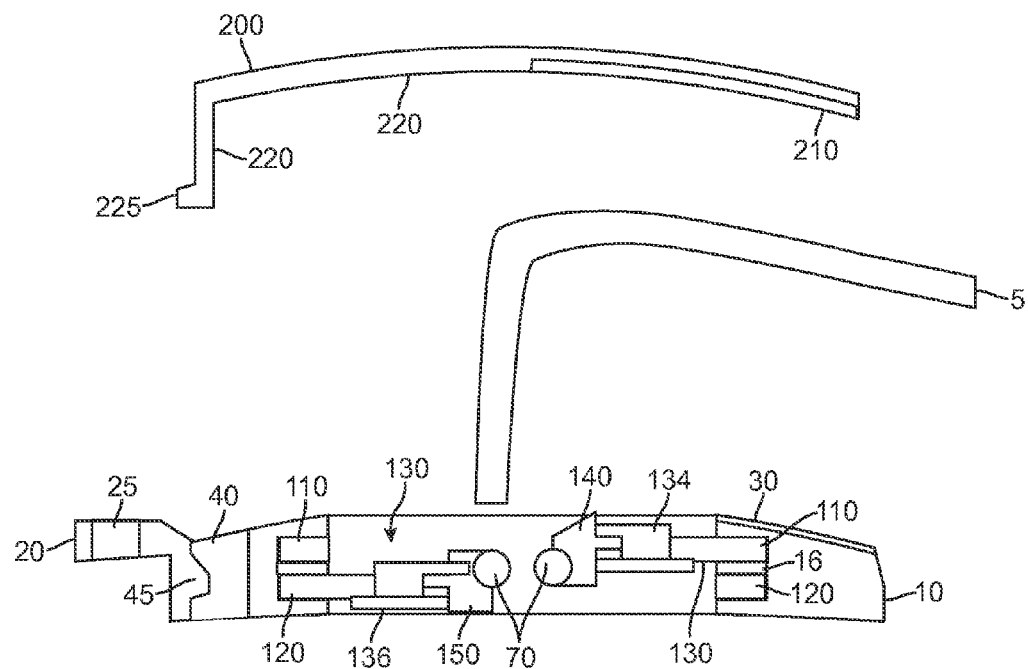
FIGS. 1A-1D illustrate cross-sections of several anchor assembly embodiments having fixation tabs that allow the anchor to be placed within a craniotomy at varying depths.

In the drawings like numerals describe substantially similar components. Now turning to FIG. 1A is a cross section exploded view of the anchor assembly, showing the probe 5, cap 200, and cylinder body 10, also referred to as an anchor base in this application, assembled with parts that grip the probe. In this embodiment, the radial tabs 20 are elevated relative to the bottom surface of base 10 so that the cylinder body 10 may be recessed into a craniotomy. The cylinder 10 is fixed to the cranium by screws which pass through openings 25 in tabs 20 and secure the tabs to the cranium. In an alternative embodiment, the cylinder may have ridges, protrusions or other surface features (not shown) which generate a friction fit with the wall of the craniotomy, in conjunction with or in lieu of the radial tabs. Rotating doors 110 and 120 are shown rotated to a position such that the grip bars 70 are positioned to grip the probe 5. In the section shown in FIG. 1A, the grip bars 70 are positioned by removable inserts 140 and 150, which in turn are captured in the doors 110 and 120 by rotating rivets 130. An upper rivet plate 134 and a lower rivet plate 136 coupled to rivet 130 help lock the inserts into position. A ring-like spacer 16 separates doors 110 and 120. The cap 200 has legs or pins 220 with catches 225 which snap into receiving sockets 40 within the cylinder 10. The receiving sockets 40 not only provide fixation for a cap, but also provide a site and mechanism for attaching other instruments to the device. Examples of other devices that could be attached thereto include positioning guides or other reference instruments commonly used during neurosurgery.

The grip bars 70 may be made of a soft material, for example an elastomer, such as silicone rubber, polyurethane, or Santoprene™, or they may be made of the same material as the doors. Grip bars 70 may be porous or have holes running through them to make them compressible. Pores could be produced by many methods, including gas bubbles forming during the curing process, dissolving filler materials, or by withdrawing filaments introduced at the time the bars are formed or molded. During implantation, the probe 5 is placed intracranially, and the rotating doors 110 and 120 are rotated to place the grip bars 70 against the probe 5. The probe 5 is bent to course along a groove 30 on the superior surface of the cylinder 10, and onto the surface of the cranium. The cap 200 is then lowered so that pins of the cap 220 are inserted into sockets of the cylinder 40, and the cap presses against the probe 5. In some embodiments, a groove in the cap 210 wraps around the probe 5. As the cap is lowered, pins 220 and protrusions from the pins 225 are displaced towards the center of the cylinder by catches 45, until the protrusions snap outward under the catches, retaining the cap. In other embodiments, the cap may have an elastomeric gasket shaped so as to seal the space between the cap and the base, except for allowing passage for the probe through one set of grooves 30 and 210. In other embodiments, the elastomeric gasket shall leave all sets of grooves open, and the unused probe passages are filled with separate plugs with radial dimension similar to the probe.

Figure 1B:
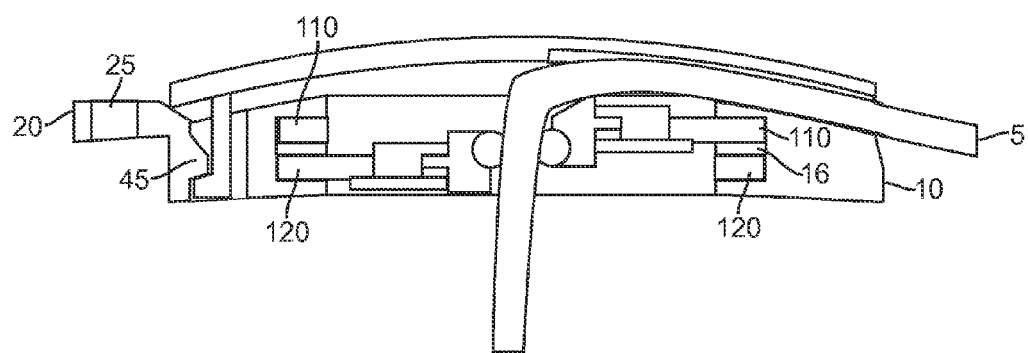

FIG. 1B shows the embodiment of FIG. 1A with the probe 5 positioned intracranially, and the cap 200 snapped into the closed position. In this embodiment, the tabs 20 are elevated so that cylinder 10 may be recessed in the craniotomy allowing the top of the cylinder to be substantially level with the cranium. Such an embodiment has the advantage that the top of the cap extends minimally above the cranium.

Figure 1C:
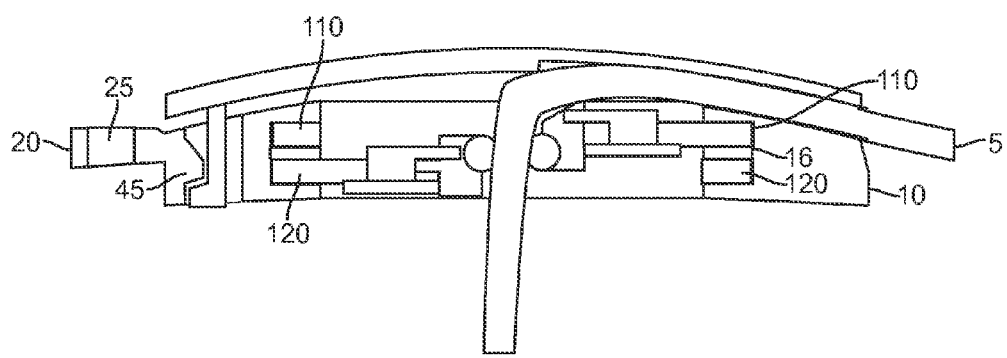
Figure 1D:
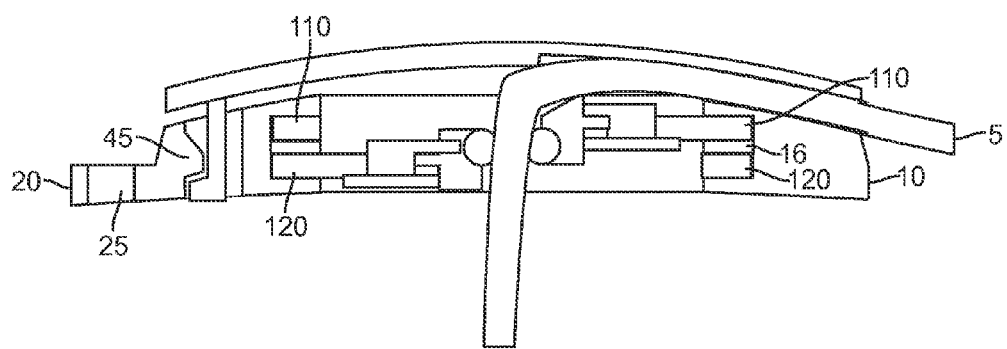

FIG. 1C shows an alternative embodiment of the assembly shown in FIGS. 1A-1B, in which the cylinder 10 is partially recessed into the cranium. FIG. 1D shows an alternative embodiment of the assembly shown in FIGS. 1A-1C, in which the tabs 20 are positioned so that the lower surface of the cylinder 10 is at the level of the outer surface of the cranium. Such an embodiment has the advantage that the craniotomy opening need only be as large as the inner lumen of the cylinder 10. The rotating door grip mechanism provides the particular advantage that if the probe 5 is inserted through the center of the device as shown in FIG. 1B, the doors may be rotated together, thereby rotating the probe while still retaining vertical fixation.

Figure 1E:
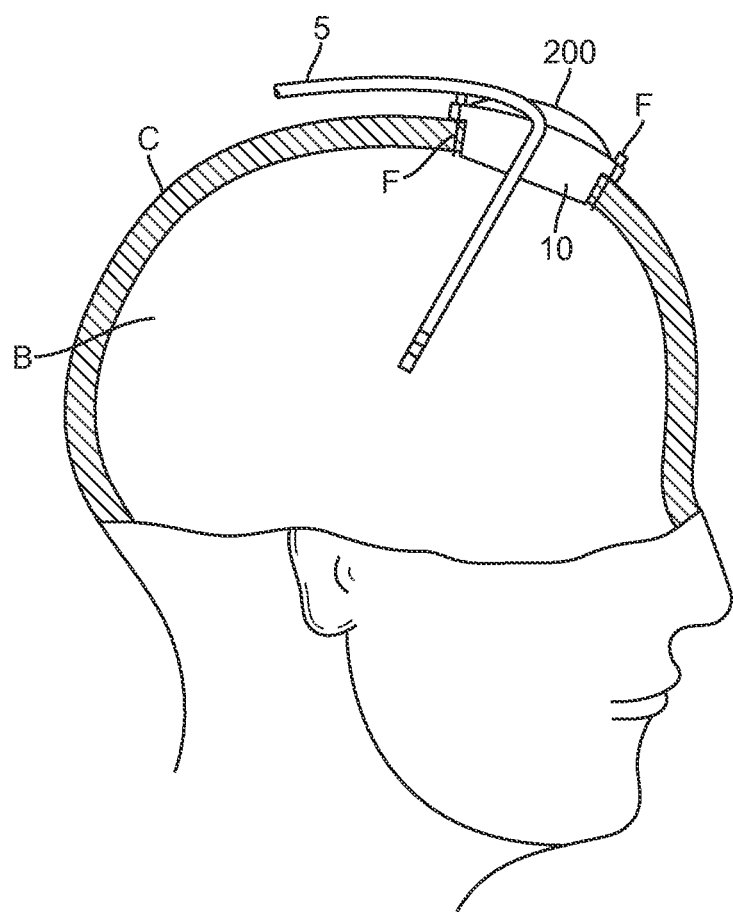
FIG. 1E shows an anchor attached to a patient's cranium.

FIG. 1E illustrates the anchor base or cylinder 10 attached to a patient's cranium C. In FIG. 1E, anchor 10 is positioned over a craniotomy so that a portion of the anchor fits within the craniotomy opening in order to reduce the portion of anchor 10 protruding out of the patient's cranium C. Fixtures F such as screws removably couple the anchor 10 to the cranium and a lead 5 is place through the central opening of the anchor 10 into the patient's brain B. A cover 200 may then be snap fit into engagement with the anchor 10, thereby capturing the lead 5 in a desired position.

Figure 2A:
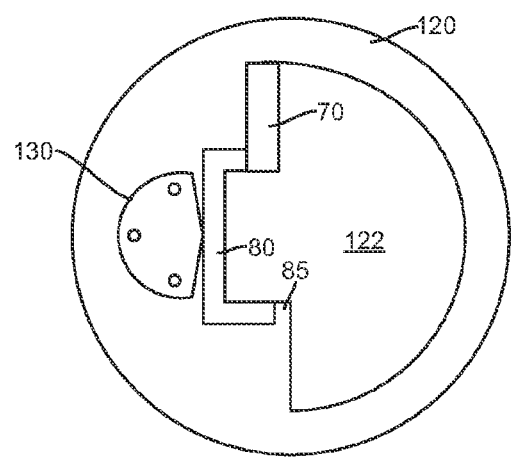
FIGS. 2A-2G show top and cross section views of rotating doors.
Figure 2B:
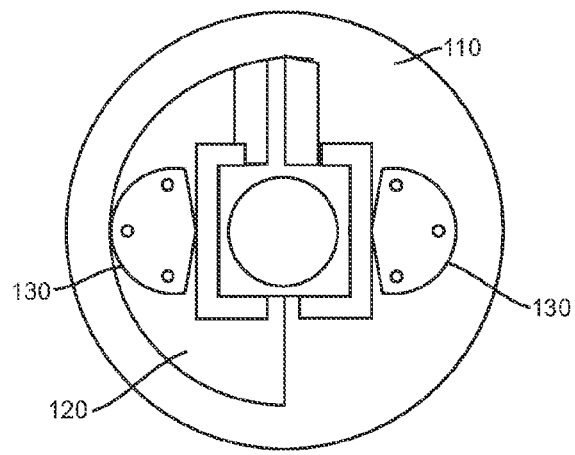

FIG. 2A shows the lower rotating door 120, apart from the rest of the anchor. The door is a disk with a large cutout 122 within its interior. Along one edge of the cutout is a bar 70 which can grip the probe placed in an intracranial position. Near the bar is a ledge depressed into the door 80 into which a gripping insert can be placed. The insert is retained from movement towards the open portion of the disk by terminating the depression at two stops 85. FIG. 2B shows both rotating doors overlayed, with the both rivets 130 in the open position and both inserts removed. In this configuration a relatively large opening in the center of the anchor is available for the probe or any related test or accessory instrumentation.

Figure 2C:
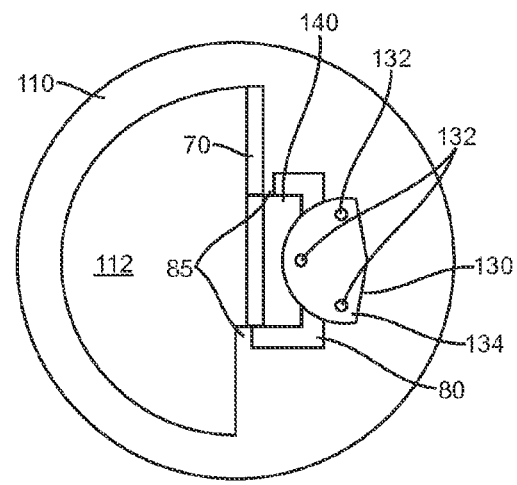

FIG. 2C shows the upper rotating door 110 with the rivet 130 in the closed position, and gripping insert 140 in place. The upper door also has a cutout 112, a gripping bar 70 and a place for seating the insert. The insert 140 rests on the depressed ledge 80. Motion of the insert towards the open part of the door 140 is prevented by the stops 85, as in the lower door. Motion of the insert up out of the ledge, or rotation of the insert out of the ledge is prevented by the rivet 130. The upper plate of the rivet 134 is a partial disk. When it is in the closed position, as shown in FIG. 2C, the upper plate covers the edge of the insert, so that it is locked into place on the depressed seating ledge 80. When it is open, the insert may be removed. The upper plate has three sockets 132 which may accept prongs from an insertion and removal tool, in order to rotate the rivet. A lower plate of the rivet 136 is similar to the upper plate 134 and also helps hold the insert. Lower plate 136 may be seen in FIG. 1A.

Figure 2E:
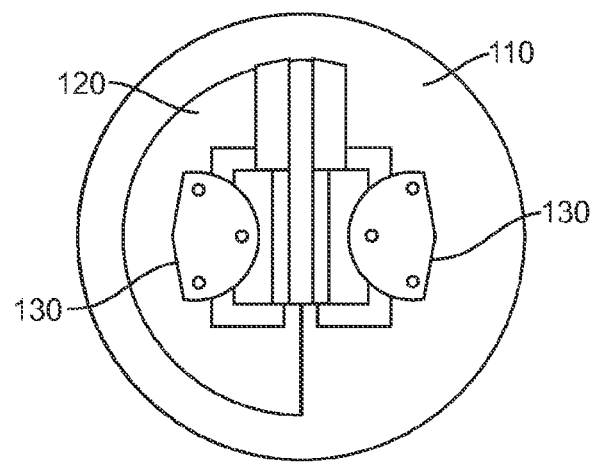
Figure 2F:
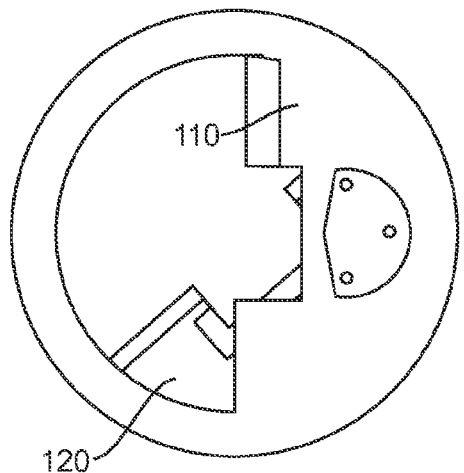
Figure 2D:
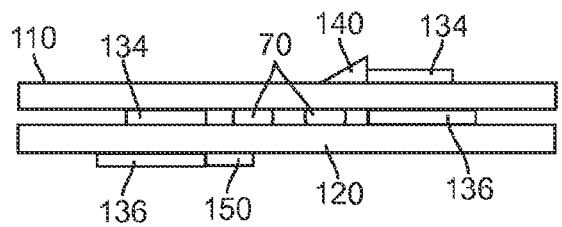
Figure 2G:
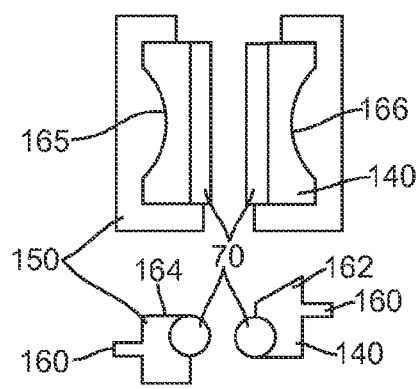

FIG. 2D shows a side view of the two rotating doors 110, 120, with the inserts 140, 150 in place, and the rivets in the closed position. When the rotating doors 110, 120 are rotated, the inserts are pushed toward each other by their corresponding doors. FIG. 2E shows the two rotating doors 110, 120 overlayed, with the inserts locked in place by the rivets 130. FIG. 2F also shows the two rotating doors overlayed, with the inserts removed and the doors opened to their maximum aperture. FIG. 2G shows both top and side views of the two inserts 140 and 150. The head or top portion 164 of insert 150 along with the head or top portion 162 of insert 140 is seen in the side view of FIG. 2G. The divots in the inserts 165, 166 accommodate the rivets. When the rivets are rotated into the closed position, the tails of the inserts 160 fit between the head of the rivet 134 and the seating depression in the rotating door 80. When the inserts are in place, their grip bars 70 are continuous with the grip bars of the rotating doors. The tails of the inserts 160 sit in recessed ledges 80 in the rotating doors.

Figure 3A:
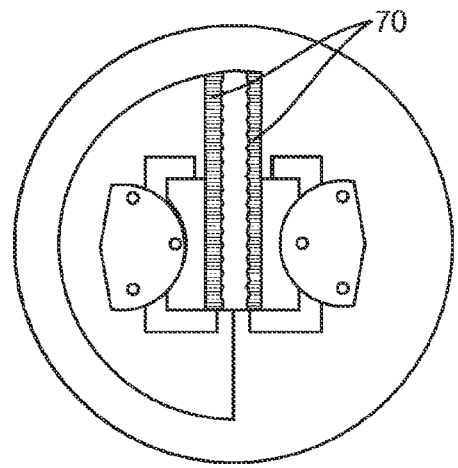
FIGS. 3A-3F show alternative embodiments of the grip bars.
Figure 3B:
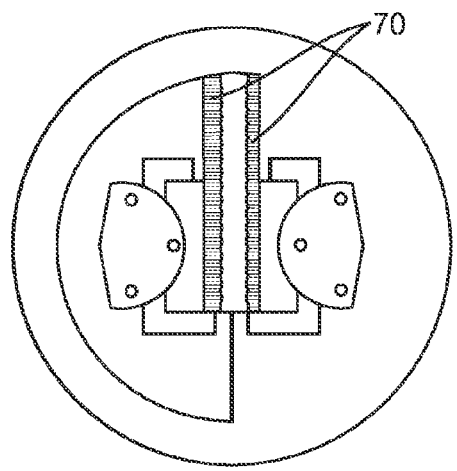
Figure 3C:
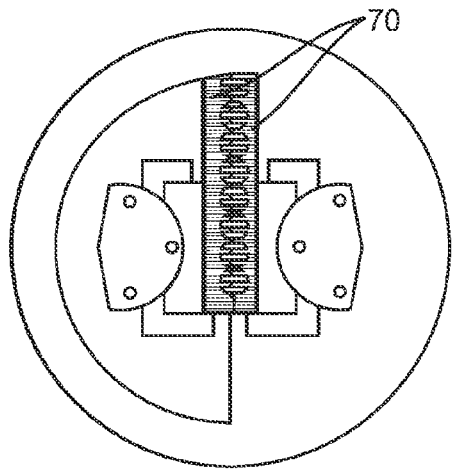
Figure 3D:
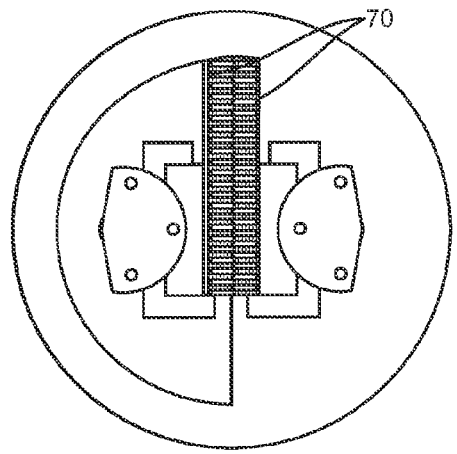
Figure 3E:
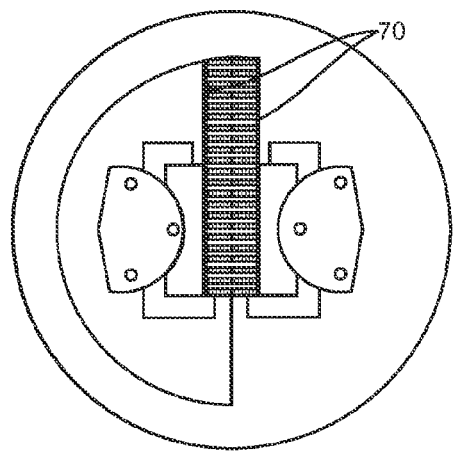
Figure 3F:
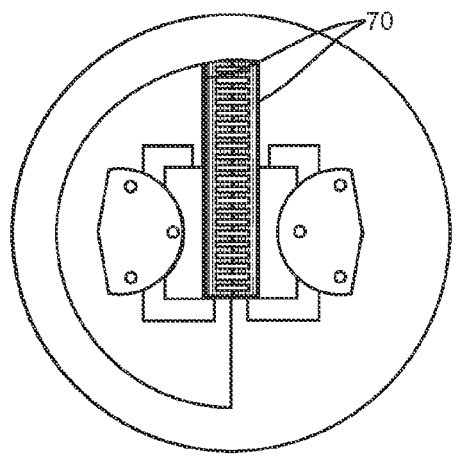

FIGS. 3A-3F show alternative embodiments of the grip bars 70, with greater contact between the grip bars and the probe compared to the embodiment shown in previous Figures. Only views from above are shown. In FIG. 3A, the grip bars are scalloped to conform to the shape of the probe, and the spacing between scallops is less than the diameter of the probe, allowing many prospective positions where the probe could be placed. In FIG. 3B, the grip bars are also scalloped, but with a shape complementary to the shape in FIG. 3A. This shape generates as many prospective positions as the shape in FIG. 3A, but instead of apposing the probe with conforming surfaces, this shape contacts the probe at 4 points, compared to two points in the embodiment shown in the other Figures. In FIG. 3C, the grip bars completely surround the probe, generating fewer prospective fixation positions compared to the embodiments of FIGS. 3A-3B. In FIG. 3D, thin flanges or resilient fingers protrude from the grip bars, such that the flanges from one grip bar are out of phase or alternate with the flanges from the other grip bar. FIGS. 3E-3F are similar to the embodiment of FIG. 3D, except that the flanges on opposite grip bars are in phase with one another so that they oppose each other, rather than the out of phase or alternating pattern seen in FIG. 3D. FIG. 3E has longer flanges, while FIG. 3F has shorter flanges. These different embodiments illustrate examples of how the contact area of the grip bar with the probe may be increased compared to the embodiments shown in the other Figures.

FIGS. 4A-4F show alternative embodiments of the grip bars 70, with one or both grip bars attached directly to the rotating door 110, 120, without an insert or the possibility of removing a portion of the grip bar 70. In FIGS. 4A-4D, the grip bars are centered on a plane between the rotating doors, as in FIG. 2D, while in FIGS. 4E and 4F, the grip bars 70 are centered in the planes of their respective rotating doors. When the grip bars are centered on a plane between the rotating doors, they do not transmit a bending moment to a probe inserted parallel to the axis of the cylindrical anchor body, while the embodiment in FIGS. 4E-4F the grip bars could potentially transmit a bending moment to such a probe.

Figure 4A:
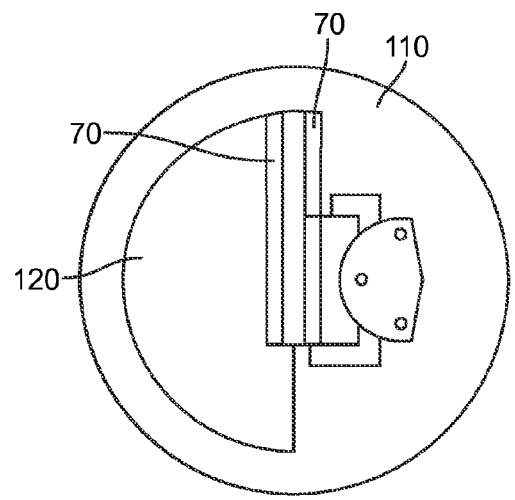
FIGS. 4A-4F show alternative embodiments of the rotating doors.
Figure 4B:
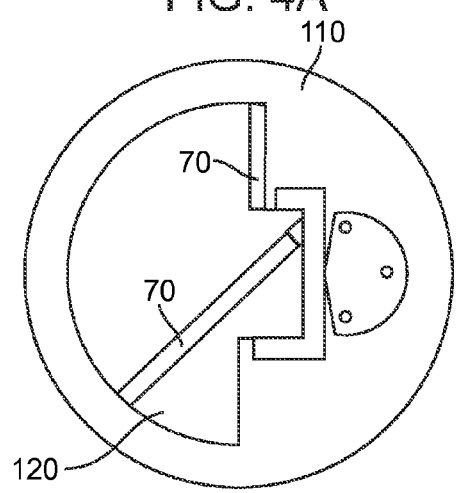

FIGS. 4A-4B show an embodiment with an upper rotating door 110 similar to the embodiments shown in FIGS. 2A-2G, while the lower rotating door has no insert, and its grip bar is one continuous member. FIG. 4A shows the rotating doors in position to grip the probe, while FIG. 4B shows the rotating doors opened to their maximum aperture. The maximum aperture of this embodiment is nearly the same as the maximum aperture illustrated in FIG. 2F, except near the center of the cylinder.

Figure 4C:
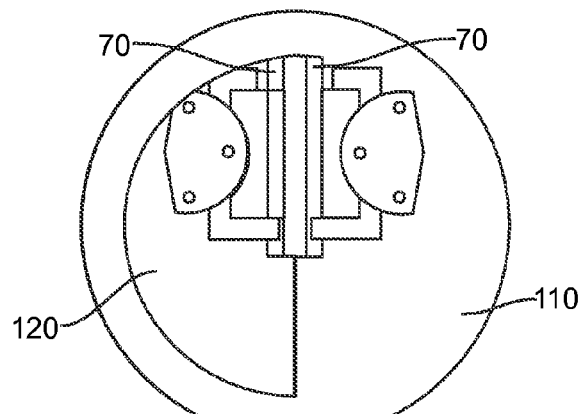
Figure 4D:
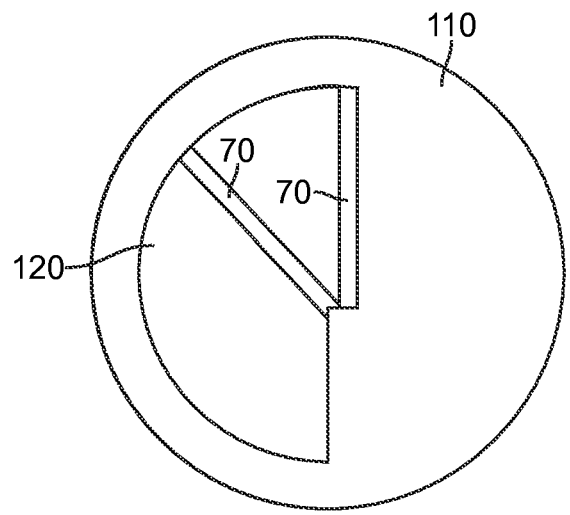

FIGS. 4C-4D, show an embodiment in which neither rotating door has an insert, and both grip bars are single, continuous members. FIG. 4C shows the rotating doors in position to grip the probe, while FIG. 4D shows the rotating doors opened to their maximum aperture. In this embodiment, the maximum aperture is smaller than in the embodiments of FIGS. 2A-2G and FIGS. 4A-4B.

Figure 4E:
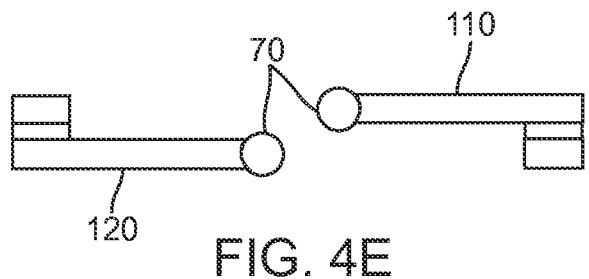
Figure 4F:
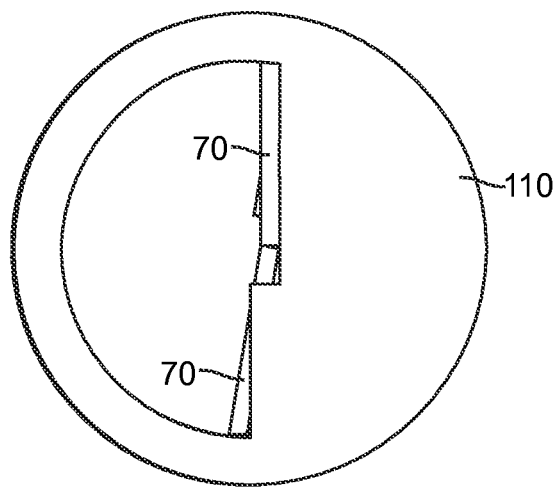

FIGS. 4E-4F show an embodiment in which neither rotating door has an insert, and both grip bars 70 are single, continuous members, as in FIGS. 4C-4D. FIG. 4E is a cross section view, which shows that in this embodiment the grip bars 70 are centered in the plane of their respective rotating doors. FIG. 4F shows that the maximum aperture of this embodiment is wider than any of the other illustrated embodiments, except near the center.

In other embodiments, the grip bars could be attached directly to the rotating doors for their full length, without any inserts or rivets. It will be obvious to those skilled in the art that many other specific forms are possible.

Figure 5A:
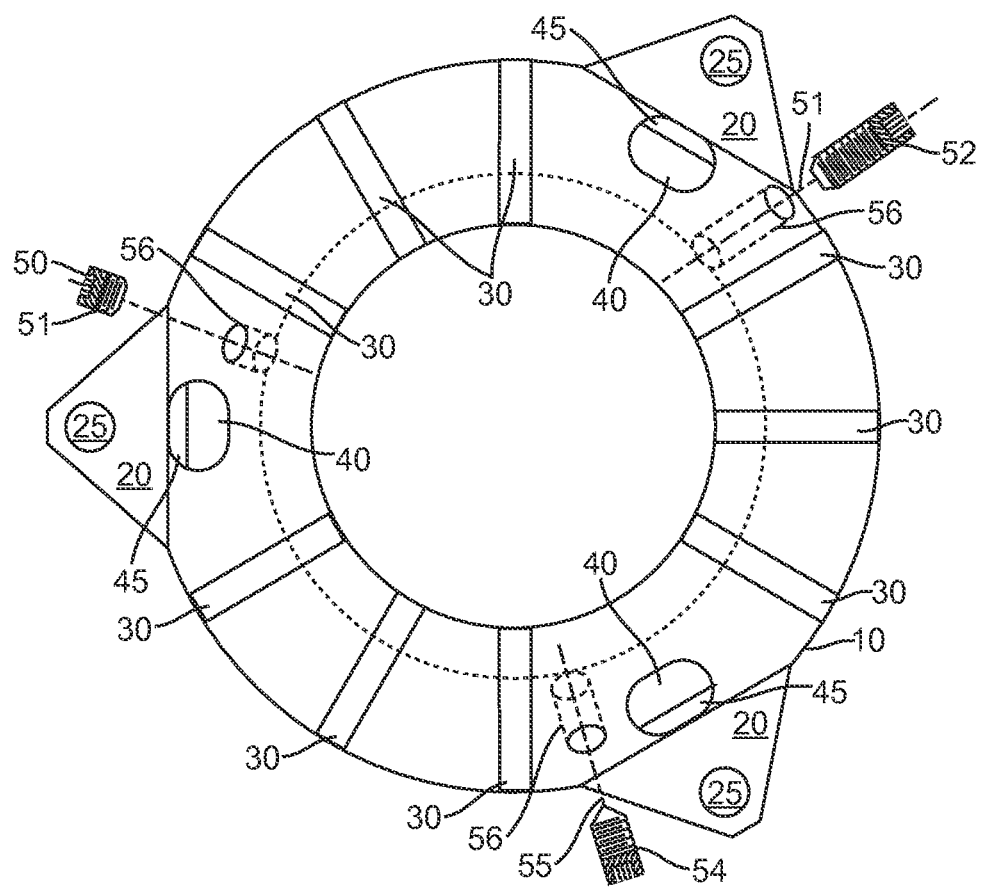
FIG. 5A shows a top view of the cylinder without the rotating doors.

FIG. 5A shows a top view of the cylinder or anchor base 10, without the rotating doors. The anchor is fixed to the cranium by screws through screw-holes 25 in radial tabs 20. A relatively short set screw 50 inserts into a threaded hole 56 to impinge upon the upper rotating door 110, (not shown) and lock it into place. A relatively long set screw 52 having a flat point 51 inserts into a threaded hole 56 to impinge upon the lower rotating door 120, (not shown) and lock it into place. Another relatively long set screw 54 having a cone point 55 inserts into a threaded hole 56 to impinge upon both rotating doors 110 and 120 (not shown) and lock them into place. In the illustrated embodiment, screws 50 and 52 have a flat tip, and impinge upon the outer upper corner of the rotating doors, while the screw 54 has an angled tip, and impinges upon the flat edge of both rotating doors. Receiving sockets 40 having catches 45 are adapted to receive the cap thereby snap fitting the two components together. Additionally, grooves or channels 30 radially extend outward from anchor 10 and provide a channel for holding the lead when the lead is captured between the anchor 10 and the cap.

Alternatively, one of the rotating doors could be held in place by a one-way ratcheting mechanism. In such an embodiment, a no-back pawl is a beam integrated with the anchor cylinder, in the plane of one of the rotating doors. The outer edge of the corresponding rotating door has the gear teeth. The pawl permits the gear teeth to pass freely in the direction which moves the grip bar 70 towards the probe, closing the door, but prevents the rotating door from opening Such an embodiment makes fixing the doors faster, as only one set screw must be tightened, yet still permits the opening between the doors to be adjusted to any angular position, multiple times if necessary.

Figure 5B:
FIG. 5B shows a side view of an exemplary embodiment of a cover.
Figure 5C:
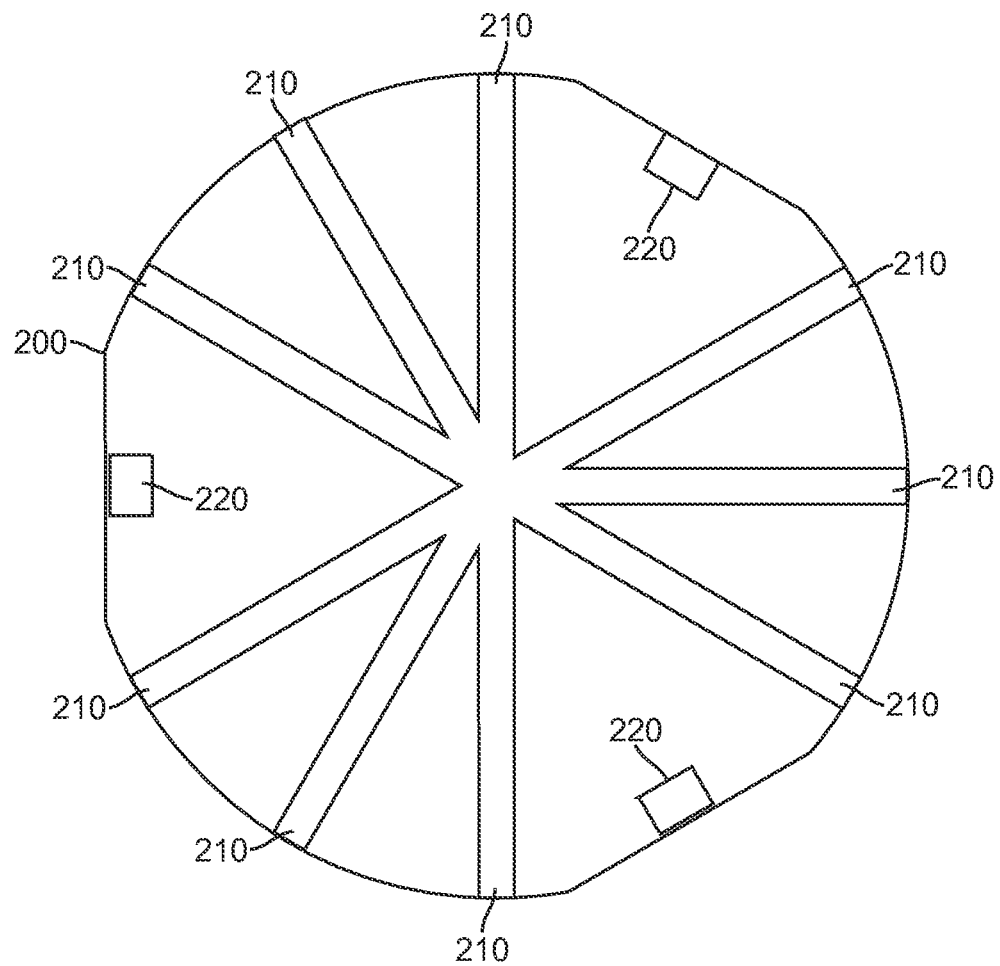
FIG. 5C shows a bottom view of an exemplary embodiment of a cover.

FIG. 5B shows a cross section view of the cap 200. It is dome shaped. Three pins 220 protrude downward, one of which is visible in this view. FIG. 5C shows a bottom view of the cap. The shape is a dome, truncated adjacent to pins 220 which protrude downward to snap into sockets 40 in the cylinder 10. The dome-shaped disk is truncated adjacent to the pins so that a tool may be inserted into the socket 40, alongside a pin 220 to facilitate removing the cap 200 when necessary. In the preferred embodiment, grooves 210 in the cap 200 increase the area of the cap 200 contacting the probe, compared to grooveless embodiments. FIG. 5C shows a bottom view of cap 200 highlighting grooves 210 and pins 220.

Initially the probe is gripped by the rotating doors and fixed into position. The probe is then bent to lay in grooves 30 on the upper surface of the cylinder. The cap is lowered, with pins 220 sliding into sockets 40 and protrusions 225 from the pins snapping into place under catches 45. When the cap is snapped in place, it presses upon the probe. In the preferred embodiment, grooves in the cap 210 increase the surface area of the cap in contact with the probe, increasing stability and decreasing point pressure on the probe.

Figure 6A:
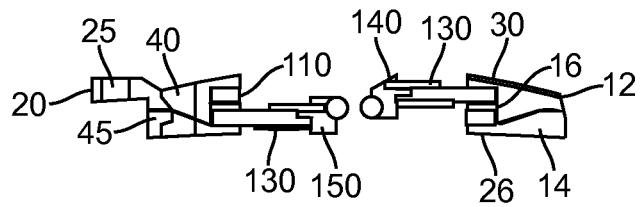
FIG. 6A shows a cross section view of an assembled anchor with rotating doors.
Figure 6B:
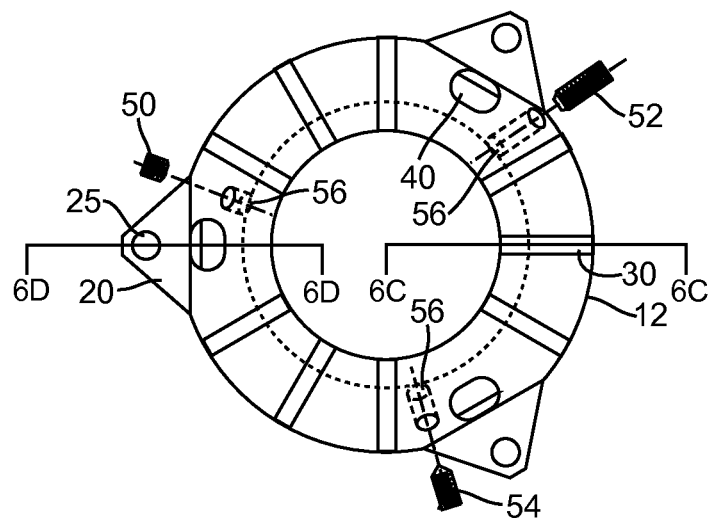
FIGS. 6B-6K show the components of the anchor depicted in FIG. 6A.
Figure 6D:
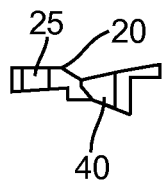
Figure 6C:
Figure 6E:
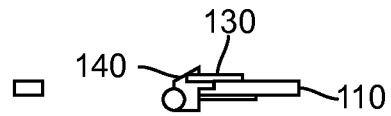
Figure 6F:
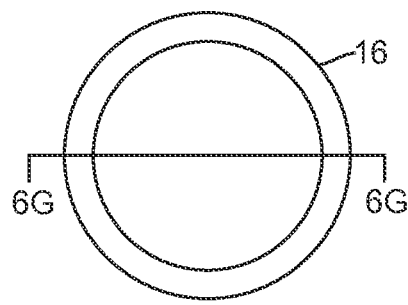
Figure 6G:
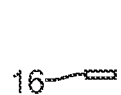
Figure 6H:
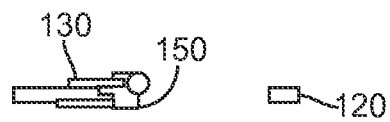
Figure 6I:
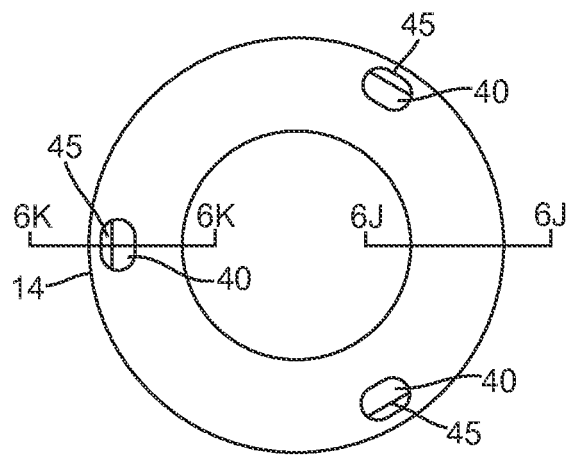
Figure 6K:
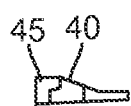
Figure 6J:

FIG. 6A shows an exemplary embodiment of an anchor base assembled with all of its components. FIGS. 6B-6K show the various components of the assembly in FIG. 6A. In FIG. 6A, the anchor base is composed of upper 12 and lower 14 portions. In the illustrated embodiment, radial tabs 20 are attached to the upper portion 12 of the cylinder 10, so that the cylinder may be recessed into the craniotomy opening In other embodiments the tabs may be attached to the lower portion 14 of the cylinder 10. A shelf 26, which retains the moving members within the cylinder, is integrated into the lower portion of the cylinder 14. The upper portion 12 of the cylinder is the more massive, because it must contain the threaded holes 56 for the set screws (seen in FIG. 6B). Within the cylinder the upper 110 and lower 120 rotating doors are separated by a spacer ring 16. The upper 12 and lower 14 portions of the cylinder are attached by an adhesive. In alternative embodiments, the base could be attached by welding or other mechanism of plastic deformation, by screws or other mechanisms which will be obvious to those skilled in the art. FIG. 6B shows the upper 12 portion of the anchor assembly while FIG. 6C shows a cross-section take along line 6C-6C and FIG. 6D shows a cross section taken along line 6D-6D. FIG. 6E shows the upper door 110 with insert 140 and rivet 130 that is positioned in the upper 12 portion of the anchor assembly. A spacer ring 6F is then positioned next in the anchor assembly and a cross section of ring 16 taken along line 6G-6G is shown in FIG. 6G. Next lower door 120 with rivet 130 and insert 150 is loaded into the anchor assembly. The lower 14 portion of the anchor base is seen in FIG. 6I. When the lower portion 14 is fastened to the upper 12 portion, the upper and lower doors 110, 120 and spacer 16 are captured therebetween. FIG. 6J shows a cross section of lower portion 14 taken along line 6J-6J and FIG. 6K shows a cross section of lower portion 14 taken along line 6K-6K.

Figure 7A:
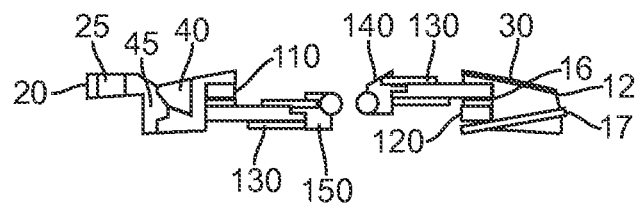
FIG. 7A shows an alternative embodiment of a mechanism for retaining the moving members within the cylinder.
Figure 7B:
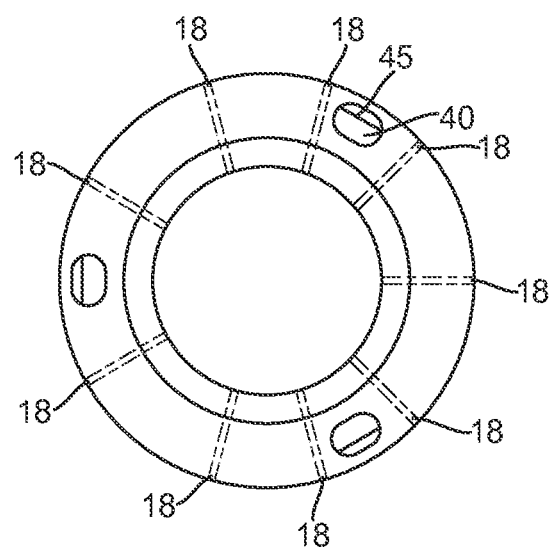
FIG. 7B shows a bottom view of the anchor assembly in FIG. 7A.

FIGS. 7A-7B show an alternative embodiment of assembling the anchor employing a plurality of pins 17 penetrating the anchor cylinder wall, and extending beneath the lower rotating door 120. The pins course through narrow channels 18 in the cylinder wall. Together, the pins provide a support that retain the moving members within the cylinder. FIG. 7A shows a cross section of the anchor assembled with all of its components and FIG. 7B shows a bottom view of the anchor base with channels 18. It is clear to those skilled in the art that this embodiment may be combined with the embodiments shown in FIGS. 6A-6I and FIGS. 8A-8M. In embodiment of FIGS. 6A-6I, the pins would provide the additional advantage of helping to retain the base of the cylinder. In the embodiment of FIG. 5, the pins provide further support for the moving members around the cutout that facilitates insertion of the rotating doors 28.

Figure 8A:
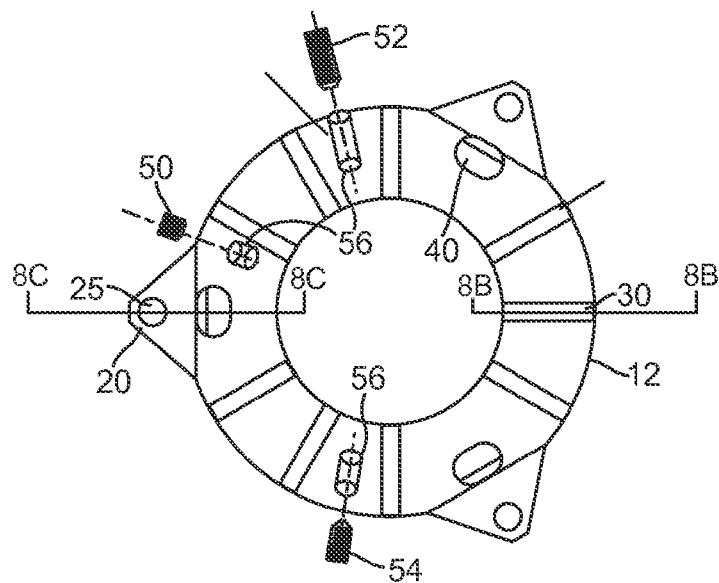
FIGS. 8A-8C show an anchor base of unitary construction.
Figure 8C:
Figure 8B:
Figure 8D:
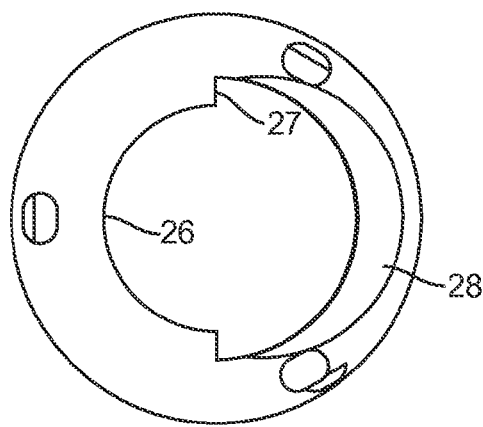
Figure 8E:
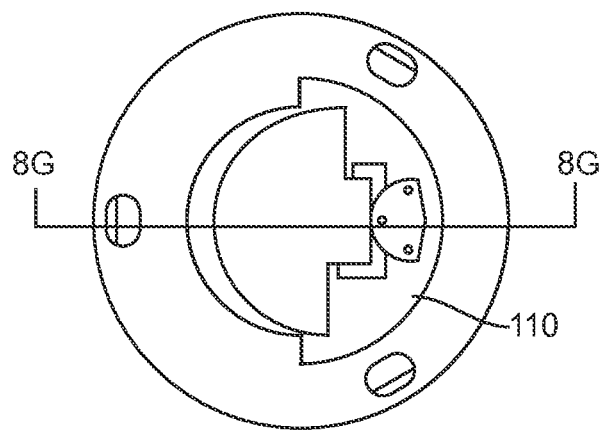
Figure 8F:
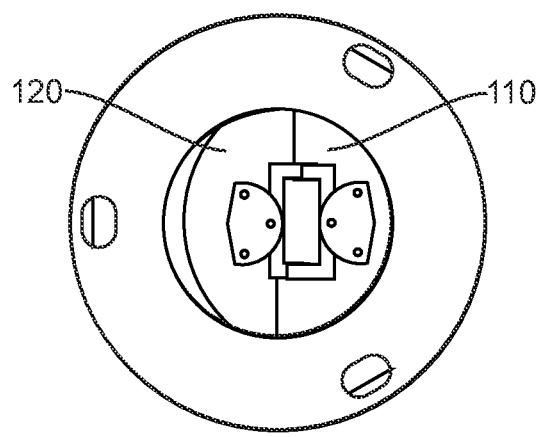

FIGS. 8A-8M show an alternative embodiment of an anchor assembly employing a different assembly method. In this embodiment, the body of the cylinder is monolithic. The bottom of the cylinder has a shelf 26 which retains the moving members. One side of the shelf is cut away 27 so that the rotating doors may be inserted from below during assembly. Such an embodiment is most compatible with a cylinder body which recesses into the craniotomy, because in such embodiments the slot is not impeded by the radial attachment tabs 20. To assemble this embodiment, the upper rotating door 110 is slid into the central chamber of the cylinder. Next, the spacer 16 is inserted below the upper rotating door. Finally, the lower rotating door 130 is inserted. One side of the bottom of the cylinder is cutout 28 to facilitate sliding the rotating doors and the spacer parts into the center of the cylinder. The rivets 130 may be attached to the rotating doors in sequence after each is inserted into the central chamber, or after both rotating doors have been inserted. The rotating doors may be prevented from exiting the central chamber by tilting the slot slightly, so that the final door is strained as it is inserted and then snaps into place, or by placing one or more pins in the slot opening so as to constrain the motion of the lower door to rotational motion only. Alternatively, in both of these embodiments, an extended shelf may be fixed in the entry slot. FIG. 8A shows the anchor base that holds the upper 110 and lower 120 rotating doors. FIG. 8B shows a cross section of the anchor base of FIG. 8A taken along line 8B-8B and FIG. 8C shows a cross section of the anchor base taken along line 8C-8C. FIG. 8D shows the bottom of the anchor base and FIG. 8E shows the anchor base after upper door 110 has been inserted into the base. FIG. 8F shows the anchor base after both upper 110 and lower 120 doors and spacer 16 have been loaded into the anchor base. FIGS. 8G-8L illustrate the sequence of loading components into the anchor base during assembly and FIG. 8M shows the assembled anchor.

Figure 9A:
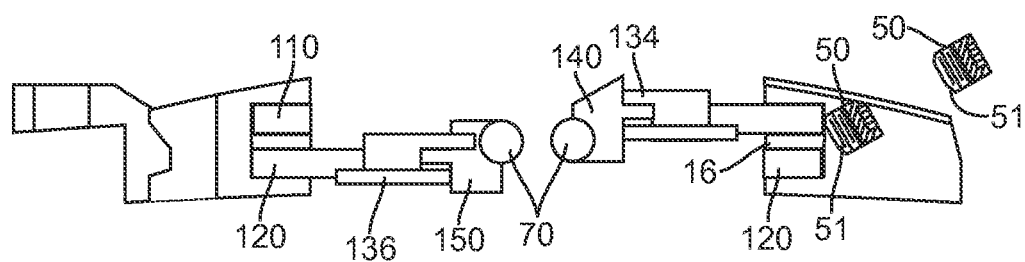
FIGS. 9A-9C illustrate the use of set screws to lock the rotating doors in position.
Figure 9B:
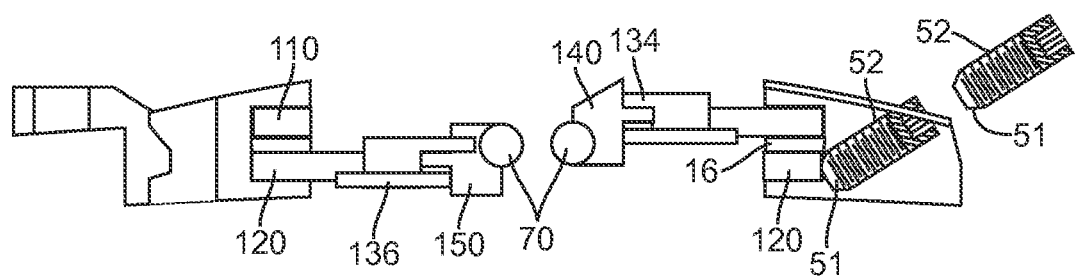
Figure 9C:
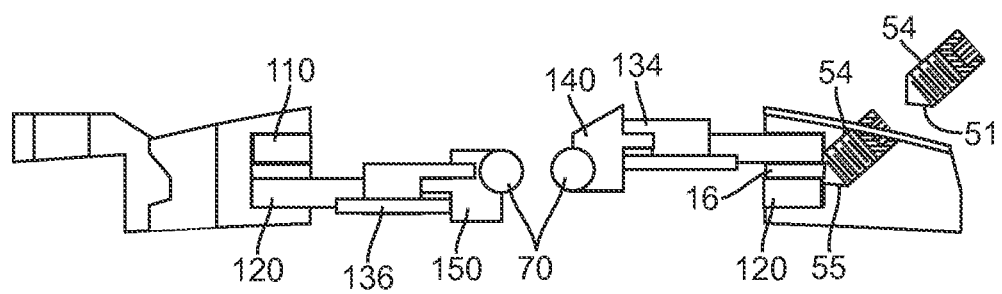

FIGS. 9A-9C show cross section views, illustrating how set screws can be positioned in three different positions, so as to impinge on the upper rotating door 110 alone, lower rotating door 120 alone, or on both rotating doors 110, 120 simultaneously. Exemplary embodiments are shown, illustrating how the rotating doors may be fixed with standard set screws. Small diameter screws, such as 0-80, are appropriate for this application, because the cylinder body 10 is thin. A thin body 10 is desired so that it does not protrude much above the surface of the cranium.

FIG. 9A shows a set screw 50 positioned to fix the upper rotating door 110. In this embodiment, a flat set screw is used. The tip of such a screw typically has a wide flat surface orthogonal to the screw's axis of symmetry, bounded by a narrow conical ring 51. When the screw is deployed with its long axis tilted at approximately 30 degrees from horizontal, one edge of the conical ring is nearly parallel to the outer edge of the upper rotating door 110. As the screw is tightened, the conical ring 51 impinges upon the outer edge of the upper rotating door, but away from the lower rotating door 120.

FIG. 9B shows a similar set screw 52 positioned to fix the lower rotating door 120. This screw is similar to the upper door fixation screw 50, except that it is longer. FIG. 9C shows a set screw 54 positioned so as to impinge upon both rotating doors 110 and 120 simultaneously. In this embodiment a cone-point set screw is illustrated. Such a set screw has a wide conical ring 55 terminating at the tip of the screw, with a tip angle of approximately 118 degrees. When the screw 54 is deployed with its long axis tilted approximately 60 degrees from horizontal, it fixes both rotating doors.

FIGS. 10A-10J show an insertion tool 300 with handle 350 for placement and removal of inserts 140 and 150 into the rotating doors 110 and 120. FIGS. 10A-10F show portions of the tool 300 from several views. A side view of the tool is seen in FIGS. 10A-10C and the tool is seen from a top view in FIGS. 10D-10F. FIGS. 10A and 10D show only the lowest portion, which interfaces directly with the insert, rotating door, and upper plate of the rivet. An orienting edge 320 at the bottom of the tool is complementary to the shape of the upper plate of the rivet 134. Tabs 310 at the bottom of the tool fit precisely into matching sockets 132 in the upper portion of the rivets. In an alternative embodiment of the tool and the top of the rotating rivet, the tabs 310 are slightly larger at their lower most position, and/or the sockets 132 are narrower at their upper most position, to facilitate a snap fit of the tool with the rivet rotor.

FIGS. 10B and 10E show a platform 340 at the base of the insertion/removal tool. The platform forms a bridge between the small features and tight tolerances of the components shown in FIGS. 10A-10B, and the grip or handle 350 through which the surgeon applies torque, is shown in FIGS. 10C and 10F. In the embodiment illustrated, the grip 350 is a hexagonal post with an angled handle, which may be turned digitally or with a wrench. In other embodiments, the grip may take another form, for example, a cap screw. In another embodiment, it could be a cylindrical post, with one or a plurality of radial holes into which a lever arm can be inserted.

FIGS. 10G-10J show how the tool mates to the upper plate of the rivet 134 and couples with an insert 150 on lower rotating door 120. The lower portion of the tool has an angled shape 320 complementary to the edge of the upper plate of the rivet 134, to facilitate alignment of the tool with the rivet, and to apply torque to the rivet as the tool is rotated. For fine positioning and additional torque, the tool has tabs 310 which insert into matching divots in the upper plate of the rivet 132. A curved pin 335 holds an insert 140 or 150 in position next to the tool 300 while the insert is placed into or removed from a rotating door 110 or 120. A bulge 330 is provided for mounting the pin 335. This mounting bulge 330 is positioned so that it does not impinge upon the upper portion of the insert 140 as the tool is rotated.

Figure 11C:
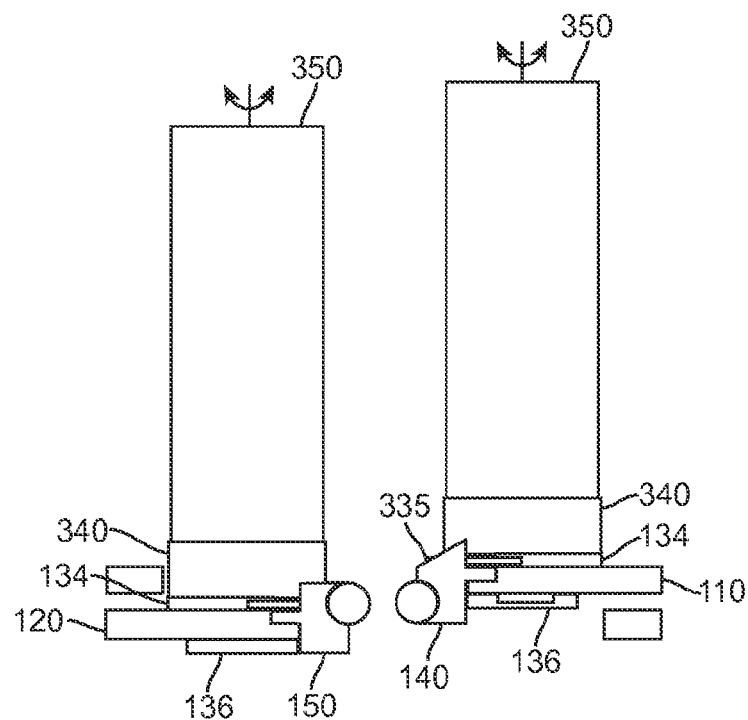
Figure 11D:
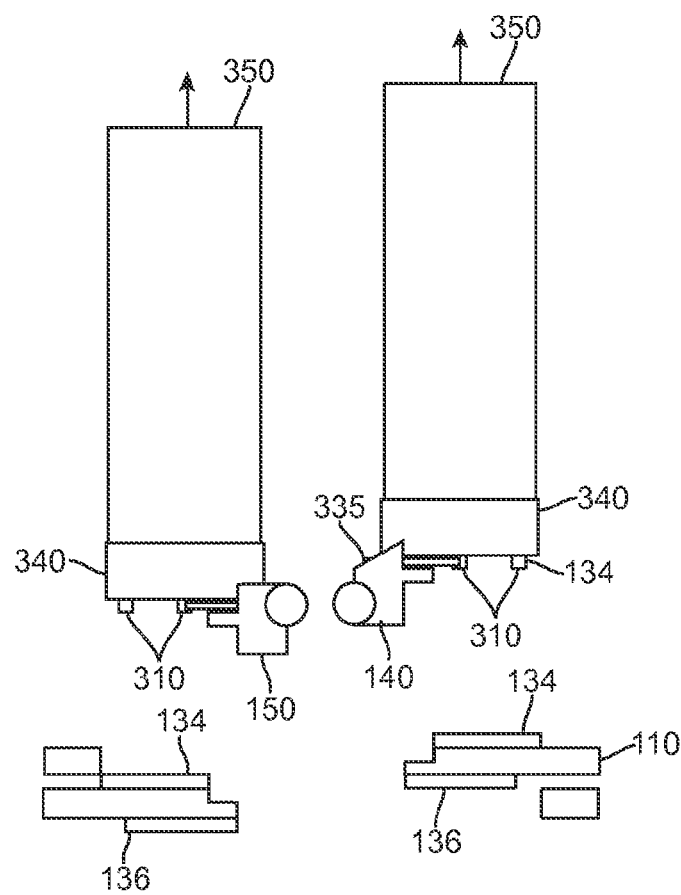

FIGS. 11A-11D show the tool and insert through the cycle of positioning, attachment and detachment. In FIG. 11A, two insertion tools are above the anchor, and the inserts are seated in the rotating doors, retained by the rivets. In FIG. 11B, the tools are lowered to a position adjacent to the upper portion of the rivets 134 and the inserts 140 and 150. The inserts are seated in the rotating doors, retained by the rivets. In FIG. 11C, the tools have been rotated as indicated by the double headed arrows, so that the holding pins retain the inserts to the bottom of the insertion tools. The rivets no longer retain inserts. In FIG. 11D, the inserts 140 and 150 are retained against the insertion tools by the holding pins 335 and lifted away from the rotating doors. The lower surface of the insertion tool fits into divots 165 and 166, (not shown) in the inserts, so that the insert has a definite position relative to the insertion tool. The rotating doors and rivets lie below the tool as the tool is lifted away.

Figure 12A:
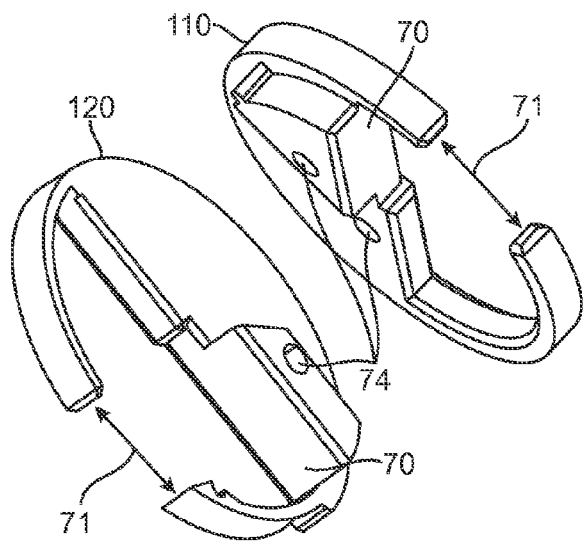
FIGS. 12A-12C show an alternative embodiment of rotating doors that are adapted to pass around a placed lead intraoperatively and snap together.
Figure 12B:
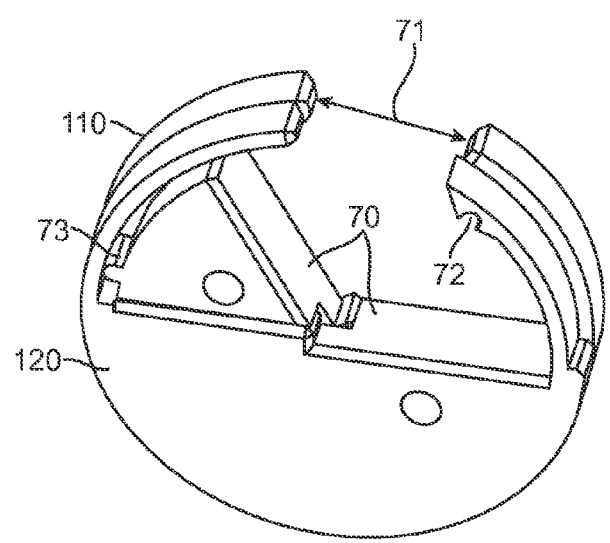
Figure 12C:
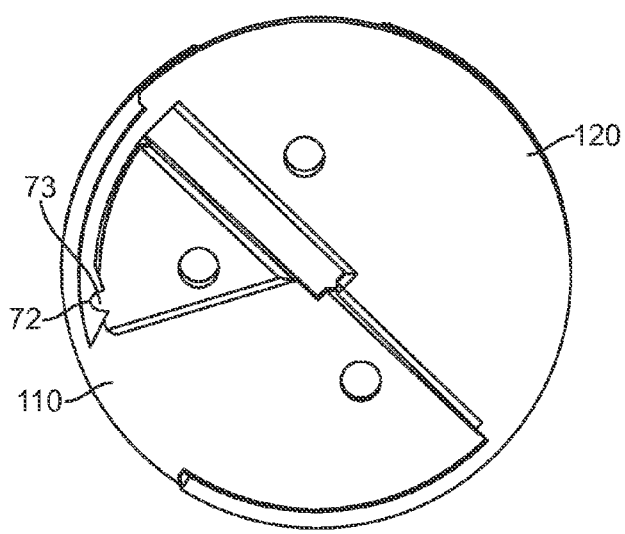

FIG. 12A-12C show an exemplary embodiment of the rotating doors adapted for intraoperative assembly. In FIG. 12A the rotating doors 110 and 120 have gaps 71 positioned so that they can be passed around an indwelling medical lead and placed in a receiving anchor base. The gaps 71 may be positioned as in FIG. 12B, so that the doors may be passed around the lead in a single movement. Intraoperative handling is facilitated by holes 74 in the doors. Once inserted into the receiving base, the doors can be rotated as in FIG. 12C in order to grip the medical lead. A snap mechanism can operate whereby a protrusion or detent from one door 73 lodges into a cavity 72 on the other, so as to maintain the doors in apposition against the lead.

Figure 13A:
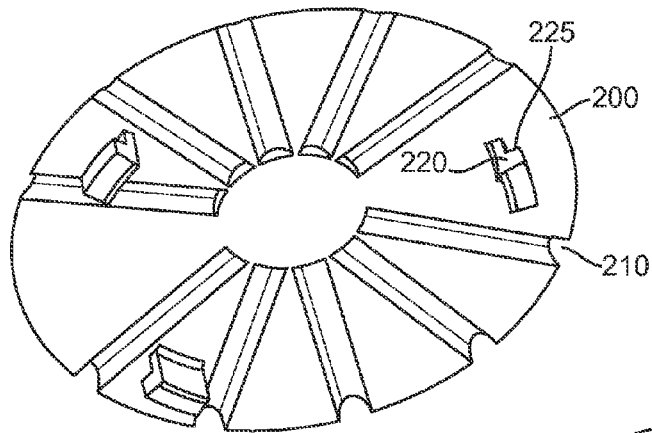
FIGS. 13A-13C show an alternative embodiment of the anchor base which may be used with the doors of FIGS. 12A-12C.
Figure 13B:
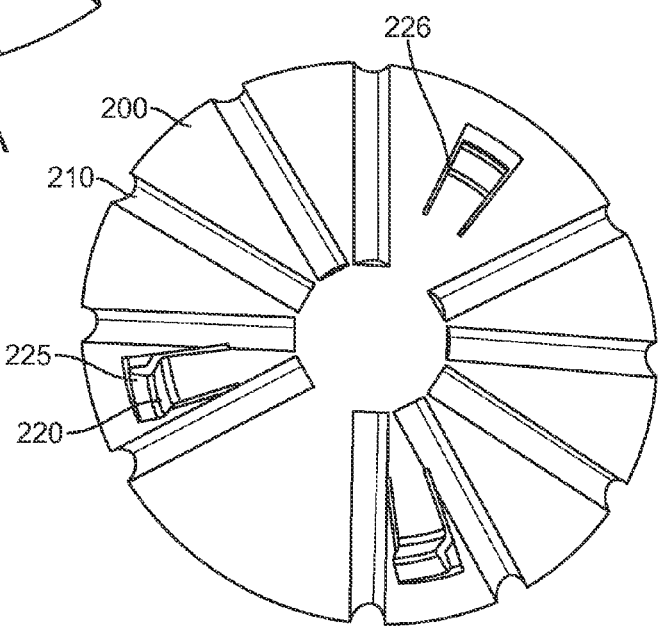
Figure 13C:
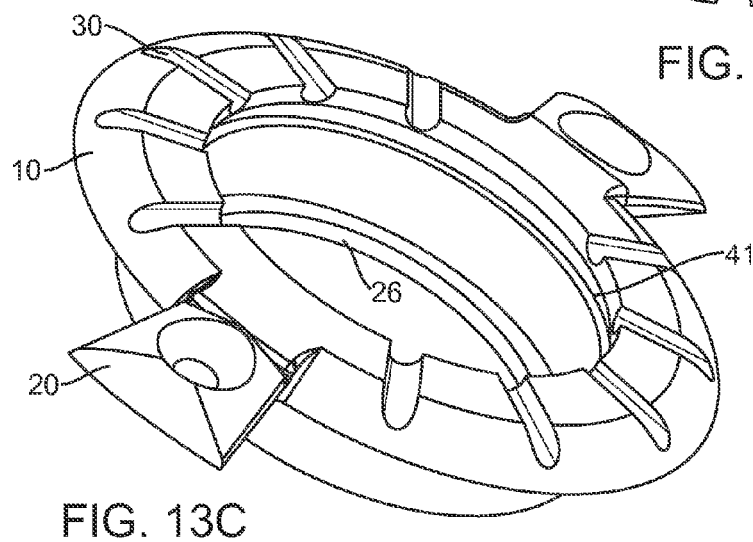

FIGS. 13A-13C show exemplary embodiments of the anchor base 10 and cap 200 adapted for intraoperative assembly with doors such as shown in FIGS. 12A-12C. In the exemplary embodiment of FIG. 13C, base 10 has two tabs 20 for attachment to the cranium, but the number of tabs may be modified as required. The doors pass around the lead, and they are placed so that the lower door rests upon a shelf 26, and the upper door rests upon the lower door. A retaining member, such as those illustrated in FIGS. 14A-14E may optionally be inserted interfacing with an annular groove 41 in such a way as to partially occlude the lumen of the base 10 and prevent removal of the rotating doors. Two embodiments of the cap 200 are shown in FIGS. 13A and 13B, with pins 220 placed so that the cap 200 can be attached to the base 10 by protrusions 225 from the pins 220 into the annular groove 41.

In the embodiment of FIG. 13B, cavities 226 are placed in the cap 200, so as to extend the effective length of the pins 220 and control the strain of the pin and mating forces, as will be familiar to those skilled in the art. The annular groove 41 can also be a point of attachment for additional instruments used intraoperatively such as a positioning guide or other reference instruments often used during neurosurgery. The retaining member may similarly be modified to permit attachment of other instruments used intraoperatively. The base 10 and cap 200 could optionally have features to force a particular alignment of the cap and base. For example, a pin may extend from the cap and seat in a groove on the base.

Figure 14C:
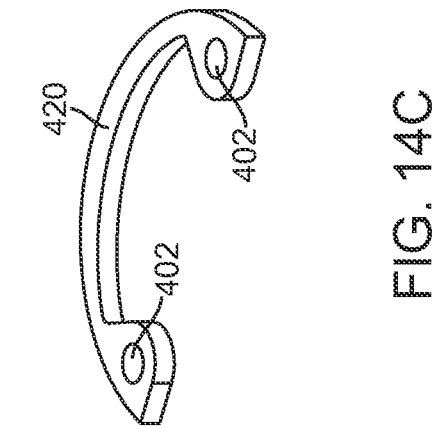
FIGS. 14A-14E illustrate exemplary embodiments of retaining members which hold the rotating doors in the anchor base.
Figure 14E:
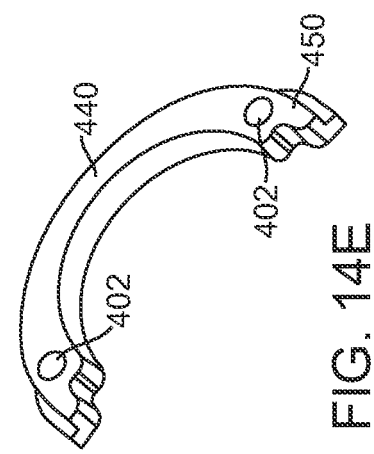
Figure 14B:
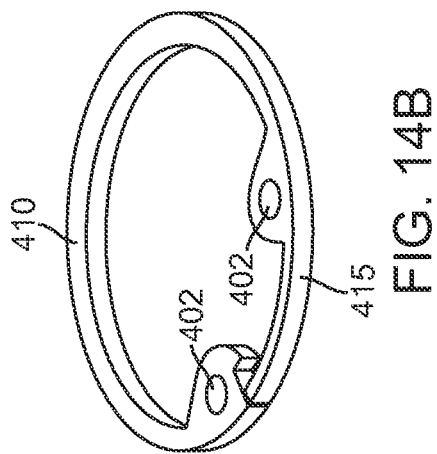
Figure 14D:
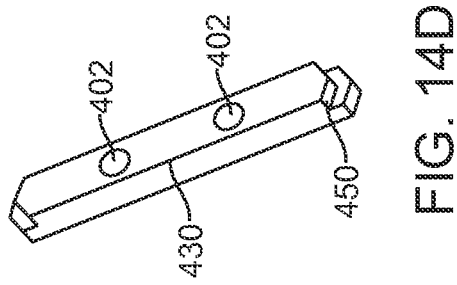
Figure 14A:
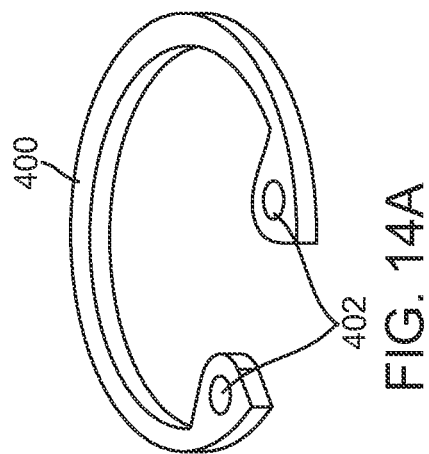

FIGS. 14A-14E show several exemplary embodiments of a retaining member which may be placed intraoperatively, so as to hold or retain the doors within the base. All of these embodiments include a hole feature to facilitate manipulation of the member. One embodiment 400 is a conventional retaining ring, as will be well familiar to those skilled in the art and this is seen in FIG. 14A. In FIG. 14B, retaining member 410 includes a member 415 to increase the security of placement of the retention member. Additional security may be desirable if mounting features for a cap or intraoperative instruments are added to the retention feature. In FIG. 14C, the retaining member 420 occupies half, more or less, of the annular groove, so as to generate less interference with a medical lead placed in the lumen of the base. In FIGS. 14D and 14E the ends of retaining members 430 and 440 interface with a groove, such as 41 of FIG. 13C, but the body of these retaining members cross through the lumen of the base. Such disposition of the body of the retaining member keeps the groove free to accept other attachments. Retaining member 430 passes straight across, while retaining member 440 curves away from the center, so that it is clear of the center during placement. The depictions of retaining members 430 and 440 also include material 450 above the plane of the annular groove. Such material may be arranged so as to strengthen or stiffen the retaining member, or to interface with other parts.

Figure 15A:
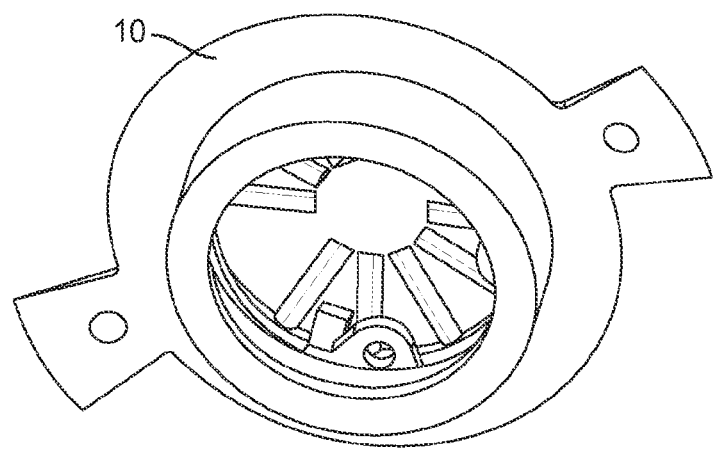
FIGS. 15A-15D illustrate an exemplary embodiment of a retaining member which retains the rotating doors and the cap.
Figure 15B:
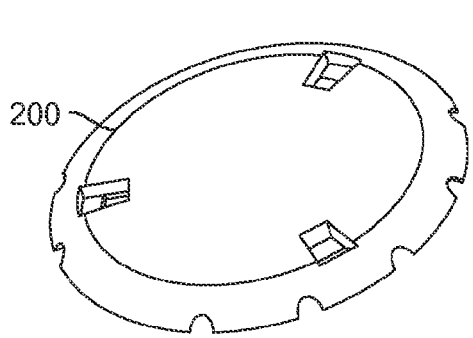
Figure 15C:
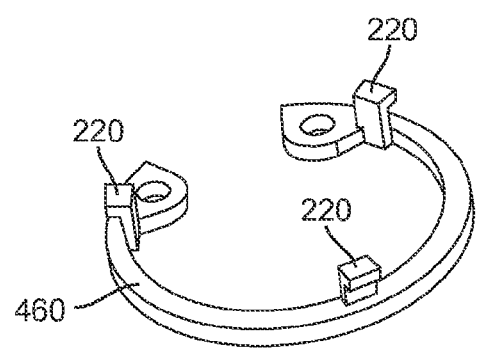
Figure 15D:
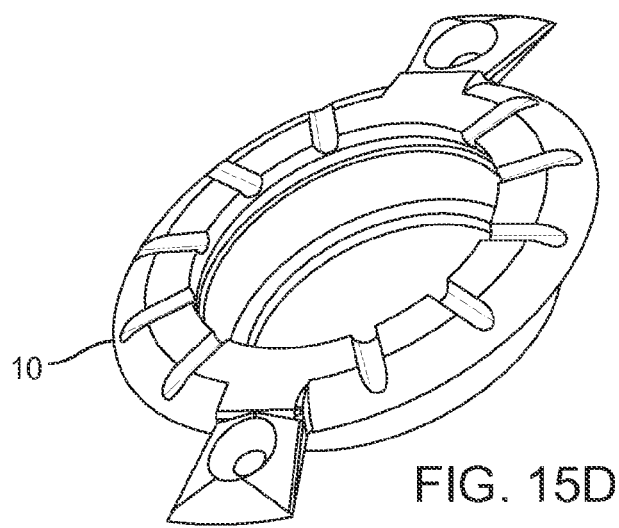
Figure 16:
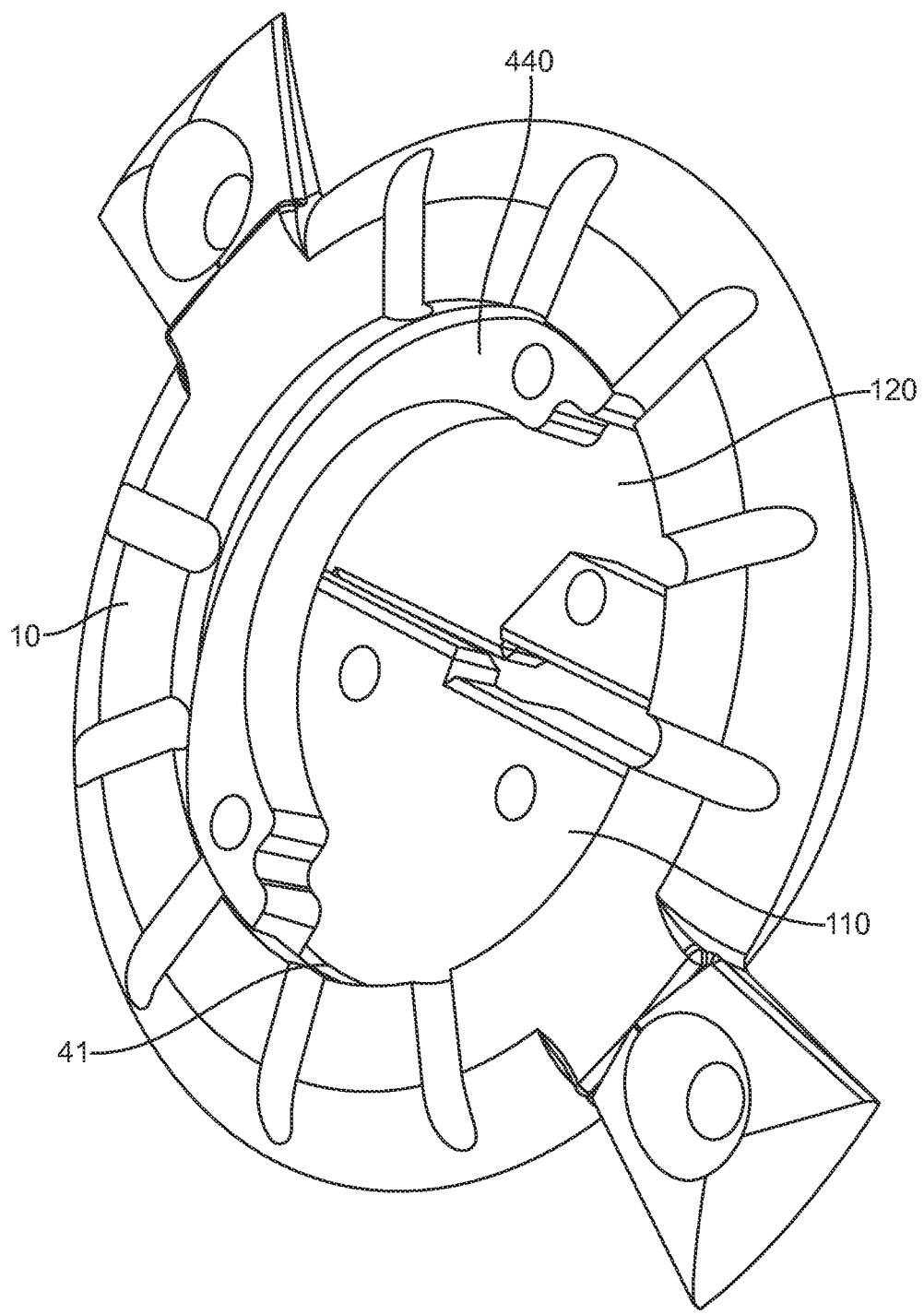
FIG. 16 illustrates an exemplary embodiment of an anchor base with rotating doors that are held in place with a retaining member.

FIGS. 15A-15D show an embodiment where retaining member 460 has pins 220 extending in such a way that they could snap into the cap 200 and thereby attach it to the base 10. FIG. 15A is a perspective view of the anchor base 10 with retaining member 460 and cap 200 assembled together. FIG. 15B shows cap 200 and FIG. 15C shows the retaining member 460. Anchor base 10 is seen in FIG. 15D. FIG. 16 is a perspective view of anchor base 10 with the doors 110 and 120 and retaining member 440 assembled together. The retaining member 440 seats into an annular groove 41, but its body is within the center of the base, leaving much of the groove 41 clear.

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. A method of securing an implantable lead into tissue of a patient, the method comprising:
   positioning a base having an upper surface, a lower surface and a central passage with a central axis therebetween adjacent a craniotomy in a skull of the patient;
   securing the base to the skull;
   inserting an implantable lead through the central passage and into the tissue;
   rotating a first rotating member coupled with the base so as to meet and engage the implantable lead at a plurality of positions within the central passage, wherein the first rotating member rotates around the central axis; and
   rotating a second rotating member coupled with the base so as to meet and engage the implantable lead at a plurality of positions within the central passage, wherein the second rotating member rotates around the central axis,
   wherein the first and second rotating members rotate independently of one another, and
   wherein rotating the first rotating member in a first direction and rotating the second rotating member in a second direction opposite the first direction engages and captures the implantable lead therebetween.

2. A method according to claim 1, further comprising rotationally adjusting the first and second rotating members in order to capture the lead therebetween or to release the lead therefrom.

3. A method according to claim 1, further comprising removing an insert coupled to the first or second rotating members, the insert releasably coupled with the lead.

4. A method according to claim 1, further comprising attaching an insert to the first or second rotating members, the insert releasably coupleable with the lead.

5. A method according to claim 1, wherein securing the base comprises press fitting at least a portion of the base into the craniotomy.

6. A method according to claim 1, wherein securing the base comprises coupling the base to the skull with a fastener.

7. A method according to claim 6, wherein the fastener is a screw.

8. A method according to claim 1, wherein securing the base comprises recessing at least a portion of the base in the craniotomy.

9. A method according to claim 1, wherein securing the base comprises coupling the base adjacent to the craniotomy so that a bottom surface of the base is substantially flush with a top surface of the skull.

10. A method according to claim 1, further comprising placing a cover into engagement with the base so as to substantially cover the central passage and capture the implantable lead therebetween.

11. A method according to claim 1, wherein the implantable lead comprises an electrode.

12. A method according to claim 1, wherein the implantable lead is a catheter.

13. A method according to claim 1, further comprising retaining the first rotating member within the base.

14. A method according to claim 13, wherein the step of retaining comprises placing a retaining member in the base.

15. A method according to claim 1, further comprising locking the first and second rotating members together so as to prevent relative motion therebetween.

16. A method according to claim 15, wherein locking the first and second rotating members comprises threadably engaging the first and second rotating members with a set screw.

17. A method according to claim 1, further comprising positioning the lead into a channel in the upper surface or a channel of the cover.

18. A method according to claim 1, further comprising applying a potting material to fill gaps between the base and the craniotomy, thereby reducing or eliminating leakage of body fluids around the base.

19. A method according to claim 1, further comprising delivering a current through the lead to the tissue.

20. A method according to claim 1, further comprising delivering a therapeutic agent through the lead to the tissue.

* * * * *